United States Patent
Lewis, II et al.

(10) Patent No.: US 10,799,441 B2
(45) Date of Patent: Oct. 13, 2020

(54) SKIN TREATMENTS CONTAINING PYRROLOQUINOLINE QUINONE (PQQ) ESTERS AND METHODS OF PREPARATION AND USE THEREOF

(75) Inventors: Joseph Abernathy Lewis, II, Chesterfield, VA (US); Joseph C. DiNardo, Vesuvius, VA (US)

(73) Assignee: PCR TECHNOLOGY HOLDINGS, LC, Richmond, VA (US)

( * ) Notice: Subject to any disclaimer, the term of this patent is extended or adjusted under 35 U.S.C. 154(b) by 0 days.

(21) Appl. No.: 14/123,238

(22) PCT Filed: Jun. 5, 2012

(86) PCT No.: PCT/US2012/040834
§ 371 (c)(1),
(2), (4) Date: Feb. 11, 2014

(87) PCT Pub. No.: WO2012/170378
PCT Pub. Date: Dec. 13, 2012

(65) Prior Publication Data
US 2014/0178316 A1    Jun. 26, 2014

Related U.S. Application Data

(60) Provisional application No. 61/493,565, filed on Jun. 6, 2011.

(51) Int. Cl.
| | | |
|---|---|---|
| *A61K 8/97* | (2017.01) | |
| *A61K 31/4745* | (2006.01) | |
| *A61K 8/66* | (2006.01) | |
| *A61Q 17/04* | (2006.01) | |
| *A61Q 19/08* | (2006.01) | |
| *A61Q 15/00* | (2006.01) | |
| *A61K 8/49* | (2006.01) | |
| *A61K 9/00* | (2006.01) | |
| *A61Q 19/00* | (2006.01) | |
| *A61K 8/9771* | (2017.01) | |
| *A61K 8/9789* | (2017.01) | |
| *A61K 8/9794* | (2017.01) | |

(52) U.S. Cl.
CPC .............. *A61K 8/4926* (2013.01); *A61K 8/66* (2013.01); *A61K 8/9771* (2017.08); *A61K 8/9789* (2017.08); *A61K 8/9794* (2017.08); *A61K 9/0014* (2013.01); *A61K 31/4745* (2013.01); *A61Q 17/04* (2013.01); *A61Q 19/005* (2013.01); *A61Q 19/08* (2013.01); *A61K 2800/522* (2013.01); *A61Q 15/00* (2013.01)

(58) Field of Classification Search
None
See application file for complete search history.

(56) References Cited

U.S. PATENT DOCUMENTS

| | | | |
|---|---|---|---|
| 4,144,325 A | 3/1979 | Voyt | |
| 4,248,861 A | 2/1981 | Schutt | |
| 7,241,461 B2 | 7/2007 | Myhill et al. | |
| 2003/0180232 A1* | 9/2003 | Ishii | A61K 8/11 424/59 |
| 2006/0171886 A1 | 8/2006 | DiNardo et al. | |
| 2008/0124409 A1* | 5/2008 | Zimmerman et al. | 424/745 |
| 2010/0261749 A1 | 10/2010 | Kamimura et al. | |

FOREIGN PATENT DOCUMENTS

| | | |
|---|---|---|
| EP | 0256472 A2 | 2/1988 |
| EP | 0305063 A2 | 3/1989 |
| EP | 1785138 A1 | 5/2007 |
| JP | 6158584 A | 3/1986 |
| JP | 63174931 A | 7/1988 |
| JP | 0578247 A | 3/1993 |
| JP | 08020512 A1 * | 1/1995 |
| JP | 0820512 A | 1/1996 |
| JP | 3625493 B2 | 3/2005 |
| JP | 2009221153 A | 10/2009 |
| WO | WO 2004064725 A2 | 8/2004 |
| WO | WO 2006102642 A1 | 9/2006 |
| WO | WO 2009133461 A1 | 11/2009 |

OTHER PUBLICATIONS

Charles Thompson, et al., "Synthesis and in Vitro Pharmacology of Substituted Quinoline-2,4-dicarboxylic Acids as Inhibitors of Vesicular Glutamate Transport", *J. Med. Chem.* Apr. 30, 2002, 45 (11) pp. 2260, American Chemical Society, Montana.

Mitsumoto, A., et al., "DJ-1 is an indicator for endogenous reactive oxygen species elicited by endotoxin," *Free Radical Res.* 35(6):885-93 (2001), School of Pharmaceutical Sciences, Kitasato University, Tokyo, Japan.

Taira, T., et al., "DJ-1 has a role in antioxidative stress to prevent cell death," *EMBO Reports* (2): 213-8 (Dec. 2004).

Chowanadisai, W., et al, "Pyrroloquinoline quinone stimulates mitochondrial biogenesis through cAMP response element-binding protein phosphorylation and increased PGC-1alpha expression," *J. Biol. Chem.* 285 (1): 142-52 Jan. 2010,The American Society of Biochemistry and Molecular Biology, Inc, USA.

(Continued)

*Primary Examiner* — David J Blanchard
*Assistant Examiner* — Sarah J Chickos
(74) *Attorney, Agent, or Firm* — Leydig, Voit & Mayer, Ltd.

(57) ABSTRACT

The present invention relates to cosmetic or dermatological compositions containing PQQ or its esters, methods of treating or promoting skin changes by topical application of these compositions, and methods of synthesis of PQQ esters. The PQQ ester-containing compositions of the present invention are unexpectedly effective in treating skin, particularly with respect to skin tolerance. When included in a topical composition, the PQQ esters of the present invention have an antioxidant effect that is useful in treating a skin change.

25 Claims, No Drawings

(56) References Cited

OTHER PUBLICATIONS

Miquel, J., "An update on the mitochondrial-DNA mutation hypothesis of cell aging," *Mutation Res.* 275 (3-6): 209-16, Sep. 1992.
Richter, C. "Oxidative damage to mitochondrial DNA and its relationship to ageing," *Int'l J. Biochem. Cell Biol.* 27 (7): 647-53, Jul. 27,1995.
Cho, DH; et al., "Mitochondrial dynamics in cell death and neurodegeneration," *Cellular and Molecular Life Sciences* 67(20):3435-47, Oct. 2010.
Tranah, G.J. "Mitochondrial-nuclear epistasis: Implications for human aging and longevity," *Ageing Res. Rev.* 10 (2): 238-52, Apr. 2011.
Duarte, J.A., "Influence of aerobic fitness on age-related lymphocyte DNA damage in humans: relationship with mitochondria respiratory chain and hydrogen peroxide production," *Age* 32 (3):337-46, Sep. 2010.
Nair, K.S. "Mitochondrial metabolic function assessed In vivo and In vitro," *Curr. Op. Clin. Nutr. Metabol. Care* 13(5):511-7,Sep. 2010.
Linnane, A.W.; Marzuki, S.; Ozawa, T.; Tanaka, M. "Mitochondrial DNA mutations as an important contributor to ageing and degenerative diseases," *Lancet* 1 (8639): 642-5, Mar. 1989.
Bliznakov, E.G. "Aging, mitochondria, and coenzyme Q(10): the neglected relationship," *Biochimie* 81(81(12)):1131-2, Dec. 1999.
Suwa, M.; et al., "Metformin increases the PGC-1 alpha protein and oxidative enzyme activities possibly via AMPK phosphorylation in skeletal muscle In vivo," *J. Appl. Physiol.* 101 (6): 1685-92, Dec. 2006.
Spindler, S.R. "Caloric restriction: from soup to nuts," *Ageing Res. Rev.* 9 (3): 324-53, Jul. 2010.
Lanza, IR; et al. "Regulation of skeletal muscle mitochondrial function: genes to proteins," *Acta Physiologica* 199(4):529-47, Aug. 2010.
Stites, T.E., et al., "Physiological importance of quinoenzymes and the O-quinone family of cofactors" *J. Nutrition* 130 (4):719-27, Apr. 2000.
Urakami, T., et al., "Synthesis of monoesters of pyrroloquinoline quinone and imidazopyrroloquinoline, and radical scavenging activities using electron spin resonance In vitro and pharmacological activity In vivo," *J. Nutr. Sci. Vitaminol.* 43(1):19-33, Feb. 1997.
Hara, H., et al., "Pyrroloquinoline quinone is a potent neuroprotective nutrient against hydroxydopamine-induced neurotoxicity," *Neurochem. Res.* 32(3):489-95, Mar. 2007.
Paz, M.A., et al., "The catalysis of redox cycling by pyrroloquinoline quinone (PQQ), PQQ derivatives, and isomers and the specificity of inhibitors," *Anal. Biochem.* 238(2):145-9, Jul. 1996.
Kumazawa, T., et al., "Levels of pyrroloquinoline quinone in various foods," *Biochem. J.* 307:331-333, Apr. 1995.
Duine, et al., Glucose Dehydrogenase From Acinetobacter Calcoaceticus A 'quinoprotein', FEBS Letters, vol. 108, Nr. 2, Dec. 1979, pp. 443-446.
Salisbury et al., "A novel coenzyme from bacterial primary alcohol dehydrogenases", Nature, vol. 280, Aug. 30, 1979, pp. 843-844.
Hauge, J.G., "Glucose dehydrogenase of *Bacterium anitratum*: an enzyme with a novel prosthetic group," *J. Biol. Chem.* 239:3630-39, May 12, 1964, USA.
Voelckel, A., et al., "Vorkommen und Photo-Isomerisierung der Urocaninsaure im Stratum Corneum bei polymorpher Lichtdermatose (PLD). Vergleichende Untersuchung bei PLD-Patienten und Hautgesunden," *Zentralblatt Haut-und Geschlechtskrankheiten* (1989), Springer-Verlag, vol. 156, Dec. 1989, pp. 1-15.
Michiels, C., Ramacle, J., "Cytotoxicity of linoleic acid peroxide malondialdehyde and 4-hydroxynonenal towards human fibroblasts," Toxicology, 66:225-234, Feb. 1990.
Deflandre, A., Lang, G. "Photostability assessment of sunscreens. Benzylidene camphor and dibenzoylmethane derivatives," *Int. J. Cosm. Sci.* 10(2):53-62, Apr. 1988.

Thiele, J.J., et al., "Depletion of human stratum corneum vitamin E: An early and sensitive In vivo marker of UV induced photooxidation," *J. Invest. Dermatol.* 110:756-761, May, 1998.
Miyachi, Y., "Skin Diseases Associated with Oxidative Injury," In: Fuchs, J., Packer, L. (eds.), "Oxidative Stress in Dermatology." Marcel Dekker, New York, pp. 323-331 (1993).
Corey, et al., "Total Synthesis of the Quinonoid Alcohol Dehydrogenase Coenzyme (1) of Methylotrophic Bacteria", J. Am. Chem. Soc., Dec. 1981, 103, p. 5599.
Gainor, et al., "Synthesis of the Bacterial Coenzyme Methoxatin", J. Org. Chem., Feb. 1982, 47, pp. 2833-2837.
Hendrickson, et al., "A Convergent Total Synthesis of Methoxatin", J. Org. Chem. Jan. 1982, 47, p. 1148.
MacKenzie, et al., "Synthesis of the Bacterial Coenzyme Methoxatin", *J. Chem. Soc., Chem. Commun.*, Dec. 1983, p. 1372.
Buchi, et al., "A Synthesis of Methoxatin", J. Am. Chem. Soc., vol. 107, Sep. 1985, 5555.
Ishii, et al., Pro-Oxidant Action of Pyrroloquinoline Quinone: Characterization of Protein Oxidative Modifications, Biosci. Biotechnol. Biochem., 74 (3), 663-666, Mar. 2010.
Nelson, et al., The Induction of Human Superoxide Dismutase and Catalase In vivo: A Fundamentally New Approach to Antooxidant Therapy, Free Radical Biology & Medicine 40 (2006) 341-347, Aug. 28, 2005.
Nunome, et al., "Pyrroloquinoline Quinone Prevents Oxidative Stress-Induced Neuronal Death Probably through Changes in Oxidative Status of DJ-1", Biol. Pharm. Bull 37(7), pp. 1321-1326, Jul. 2008.
Ohwada, et al., Pyrroloquinoline Quinone (PQQ) Prevents Cognitive Deficit Caused by Oxidative Stress in Rats, J. Clin. Biochem. Nutr.,42, Jan. 29-34, 2008.
Puehringer, et al., "The Pyrroloquinoline Quinone Biosynthesis Pathway Revisited: A Structural Approach", BMC Biochemistry 9:8, Mar. 2008.
Steinberg, et al., "Pyrroloquinoline Quinone Improves Growth and Reproductive Perfomance in Mice Fed Chemically Defined Foods", Department of Nutrition, University of California, pp. 160-166, Sep. 2002.
Stites, et al., "Pyrroloquinoline Quinone Modulates Mitochondrial Quantity and Function in Mice", Department of Molecular Biosciences (School of Veterinary Medicine), University of California, pp. 390-396, Nov. 2005.
Tao, et al., "Pyrroloquinoline Quinone Preserves Mitchondrial Function and Prevents Oxidative Injusry in Adult Rat Cardiac Myocytes", Biochem Biophys Res Commun., 363(2): pp. 257-262, Nov. 2007.
Wecksler, et al., "Pyrroloquinoline Quinone Biogenesis: Demonsration that PqqE from Klebsiella pneumonia is a Radical SAM Enzyme", Biochemistry 48(42), pp. 1-26, Oct. 2009.
MacKenzie, et al., "Synthesis of the Bacterial Coenzyme Methoxatin", Tetrahedron, vol. 42, Nr. 12, pp. 3259-3268.
Victor L. Davidson et al: "Apparent oxygen-dependent inhibition by superoxide dismutase of the quinoprotein methanol dehydrogenase", Biochemistry, vol. 31, No. 5, Feb. 1, 1992 (Feb. 1, 1992), pp. 1504-1508, XP055163318, ISSN: 0006-2960, DOI: 10.1021/bi00120a030* p. 1505; figure 2; table II*.
Mulholland et al: "Analysis of the fat-soluble vitamins using narrow-bore high-performance liquid chromatography with multichannel UV-VIS detection", Journal of Chromatography, Elsevier Science Publishers B.V, NL, vol. 350, Jan. 1, 1985 (Jan. 1, 1985), pp. 285-291, XP022522699, ISSN: 0021-9673, DOI: 10.1016/S0021-9673(01)93528-9 * figure 3*.
Kai He, et al., "Antioxidant and pro-oxidant properties of pyrroloquinoline quinone (PQQ): implications for its function in biological systems", Biochemical Pharmacology vol. 65, issue 1, Jan. 1, 2003, pp. 67-74.

* cited by examiner

SKIN TREATMENTS CONTAINING PYRROLOQUINOLINE QUINONE (PQQ) ESTERS AND METHODS OF PREPARATION AND USE THEREOF

CROSS-REFERENCE TO RELATED APPLICATIONS

This application is a U.S. National Phase application under 35 U.S.C. § 371 of International Application No. PCT/US2012/040834, filed on Jun. 5, 2012, and claims benefit to U.S. Provisional Application Ser. No. 61/493,565, filed on Jun. 6, 2011. The International Application was published in English on Dec. 13, 2012, as WO 2012/170378 A1 under PCT Article 21(2).

FIELD

The present invention relates to topical dermatological compositions containing an effective amount of a pyrroloquinoline quinone (PQQ) ester. In particular, the invention relates to compositions that provide effective protection from damaging oxidation processes in the skin, and also provide protection for the compositions themselves (including, for example, the constituents of cosmetic compositions containing these PQQ esters) from damaging oxidation processes. Furthermore, the PQQ esters of the present invention support vesicular breathing and cellular respiration, contribute to stabilization of mitochondrial membranes, and promote the regeneration and vitality of skin cells.

BACKGROUND

Skin is exposed to damage resulting from various sources, including both environmental factors and biochemical processes. Oxidative processes damage proteins, lipids, and other cellular components necessary to maintain the health and appearance of skin, resulting in skin changes, such as skin aging, hyperpigmentation, UV damage, lines, wrinkles, uneven skin texture, etc. Oxidative damage to the skin and its more detailed causes are described in Myachi, Y., "Skin Diseases Associated with Oxidative Injury," In: Fuchs, J., Packer, L. (eds.), "Oxidative Stress in Dermatology." Marcel Dekker, New York, pp. 323-331 (1993).

The damaging effects of the UV part of solar radiation on the skin are generally known. While rays having a wavelength less than 290 nm (the UVC range), are absorbed by the ozone layer in the earth's atmosphere, rays in the range between 290 nm and 320 nm (the UVB range), cause an erythema, simple sunburn or even more or less severe burns. The narrower range around 308 nm is given as a maximum for erythema activity of sunlight. For protection against UVB radiation, numerous compounds are known, including derivatives of 3-benzylidene camphor, 4-aminobenzoic acid, cinnamic acid, salicylic acid, benzophenone, and 2-phenylbenzimidazole. Also, for the range between about 320 nm and about 400 nm (the UVA range) it is important to have filter substances available, since UVA rays can cause reactions in light-sensitive skin. It has been demonstrated that UVA radiation leads to damage of the elastic and collagenic fibers of the connective tissue, which allows the skin to age prematurely, and that it is to be regarded as a cause of numerous phototoxic and photoallergic reactions. The damaging influence of UVB radiation can be amplified by UVA radiation. It has also been demonstrated that consumption of lipophilic antioxidants, for example, alpha-tocopherol, is triggered in the skin by UVA and UVB radiation. Thiele, J., Traber, M. G., Packer, L., "Depletion of human stratum corneum vitamin E: an early and sensitive in vivo marker of UV induced photo-oxidation," *J. Invest. Dermatol.* 110:756-761 (1998).

Further, UV radiation is ionizing radiation. Hence, there is the risk that ionic species are produced upon UV exposure, which are then able to intervene oxidatively in the biochemical processes.

For protection against the rays of the UVA range, certain derivatives of dibenzoylmethane have therefore been used, the photostability of which is not provided to an adequate extent. Deflandre, A., Lang, G. "Photostability assessment of sunscreens. Benzylidene camphor and dibenzoylmethane derivatives," *Int. J. Cosm. Sci.* 10(2):53-62 (1988). UV radiation, however, can also lead to photochemical reactions, wherein then the photochemical reaction products intervene in the skin mechanism.

Predominantly such photochemical reaction products are free radical compounds, for example hydroxyl radicals. Also, undefined free radical photoproducts, which are produced in the skin itself, can trigger uncontrolled side reactions due to their high reactivity. Singlet oxygen, a non-free radical excited state of the oxygen molecule, however, can occur in UV irradiation, short-lived epoxides and many others. Singlet oxygen, for example, is characterized with respect to the normally existing triplet oxygen (free radical base state) by increased reactivity. Nevertheless, excited, reactive (free radical) triplet states of the oxygen molecule also exist. Furthermore, there is the occurrence of lipid peroxidation products, such as hydroperoxides and aldehydes, wherein first in turn free radical chain reactions can be triggered and to which overall cytotoxic properties have been ascribed. Michiels, C., Ramacle, J., "Cytotoxicity of linoleic acid peroxide malondialdehyde and 4-hydroxynonenal towards human fibroblasts," *Toxicology*, 66:225-234 (1990). Lipid peroxidation is an oxidative process that degrades lipids, wherein free radicals steal electrons from the lipids in cell membranes, causing oxidative stress and cell damage.

Light-sensitive skin includes the disorder photodermatoses (photosensitive eruptions). Further designations for the polymorphic light-dermatosis are PLD, PLE, Mallorca Acne and a plurality of further designations, as are given in the literature. See Voelckel, A., et al., "Vorkommen and Photo-Isomerisierung der Urocaninsaure im Stratum Corneum bei polymorpher Lichtdermatose (PLD). Vergleichende Untersuchung bei PLD-Patienten und Hautgesunden," *Zentralblatt Haut-und Geschlechtskrankheiten* (1989), Springer-Verlag, vol. 156, 1989, pp. 1-15.

Erythematous skin symptoms also occur as concomitant symptoms in certain skin diseases or skin irregularities. For example, the typical rash in the clinical picture of acne is regularly reddened to a greater or lesser extent.

In order to prevent these reactions, additional antioxidants and/or free radical absorbers/scavengers can be incorporated in cosmetic or dermatological formulations. Antioxidants are substances that scavenge free radicals and prevent oxidation processes or prevent the auto-oxidation of fats containing unsaturated compounds. Antioxidants used in the field of cosmetics and pharmacy include, for example, alpha-tocopherol, in particular in the form of alpha-tocopheryl acetate, sesamol, colic acid derivatives, butylhydroxy anisole, butylhydroxy toluene, vitamin C, plant-derived polyphenols and flavonoids, and idebenone. Antioxidants are often used as protective substances against the decay of the compositions containing them. However, it is also known that undesirable oxidation processes can occur in the human and animal skin. Such processes play a considerable part in skin aging. Thus, antioxidants and/or free radical absorbers can additionally be incorporated into cosmetic formulations to treat or prevent damage caused by oxidative and/or degenerative biochemical processes. It has been proposed to use vitamin E (U.S. Pat. Nos. 4,144,325 and 4,248,861), a substance having known anti-oxidative action in sunscreen formulations, but even here the action achieved remains far below that hoped for. Tocopherol (a vitamin E antioxidant), for example, degrades to form pro-oxidative products.

Pyrroloquinoline quinone (PQQ) was discovered as a coenzyme of methanol dehydrogenase contained in a methanol-assimilating bacterium. See Hauge, J. G., "Glucose dehydrogenase of *Bacterium anitratum:* an enzyme with a novel prosthetic group," *J. Biol. Chem.* 239:3630-39 (1964); Salisbury, S. A., Forrest, H. S., Cruse, W. B. T., Kennard, O., *Nature,* 280:843-844 (1979); Duine, J. A., Frank, J. J., Van Zeeland, J. K., *FEBS Lett.* 108, 443-446 (1979). PQQ has been detected from microorganisms and from edible plants, such as soybeans, broad beans, green pepper, potatoes, parsley, and spinach, and processed food products, such as vinegar, tea, cocoa, natto, and tofu. See Kumazawa, T., Sato, K., Seno, H., Ishii, A., Suzuki, O., "Levels of pyrroloquinoline quinone in various foods," *Biochem. J.* 307:331-333 (1995).

The first total synthesis of PQQ was published in 1981 by Corey and Tramontano with an overall yield of 10% for 10 steps. See Corey, E. J.; Tramontano, A. *J. Am. Chem. Soc.* 1981, 103, 5599. Since then, a number of syntheses have been published. See, e.g., Weinreb, S. M.; Gainor, J. A. *J. Org. Chem.* 1982, 47, 2833; Hendrickson, J. B.; de Vries, J. G. *J. Org. Chem.* 1982, 47, 1148; MacKenzie, A. R.; Moody, C. J.; Rees, C. W. *J. Chem. Soc., Chem. Commun.* 1983, 1372 and *Tetraheron* 1986, 42, 3268; Buchi, G.; Botkin, J. H.; Lee, G.; Yakushifin, K. *J. Am. Chem. Soc.* 1985, 107, 5555.

PQQ esters have been prepared by esterification of PQQ optionally followed by partial hydrolysis to yield triesters, diesters, and monoesters. PQQ and its esters can also exist in salt form. The esterification reaction has typically been carried out using alcohols under acidic conditions, or by reaction with alkyl halide, alkenyl halide, alkynyl halide, aralkyl halide, araryl halide, in the presence of base.

PQQ has been reported to act as a free radical scavenger, capable of carrying out thousands of electron transfers without undergoing molecular breakdown. See Paz, M. A., Martin, P., Fliickiger, R., Mah, J., Gallop, P. M., "The catalysis of redox cycling by pyrroloquinoline quinone (PQQ), PQQ derivatives, and isomers and the specificity of inhibitors," *Anal. Biochem.* 238(2):145-9 (1996). In particular, PQQ has been reported to be effective in neutralizing superoxide and hydroxyl radicals. See Hara, H., Hiramatsu, H., Adachi, T., "Pyrroloquinoline quinone is a potent neuroprotective nutrient against hydroxydopamine-induced neurotoxicity," *Neurochem. Res.* 32(3):489-95 (2007); Urakami, T., Yoshida, C., Akaike, T., Maeda, H., Nishigori, H., Niki, E., "Synthesis of monoesters of pyrroloquinoline quinone and imidazopyrroloquinoline, and radical scavenging activities using electron spin resonance in vitro and pharmacological activity in vivo," *J. Nutr. Sci. Vitaminol.* 43(1):19-33 (1997). PQQ was reported to be 30 to 5,000 times more efficient in sustaining redox cycling (mitochondrial energy production) than other common antioxidants such as ascorbic acid. See Stites, T. E., Mitchell, A. E., Rucker, R. B., "Physiological importance of quinoenzymes and the 0-quinone family of cofactors" *J. Nutrition* 130 (4):719-27 (2000).

PQQ has also been reported to promote the spontaneous generation of new mitochondria within aging cells, a process known as mitochondrial biogenesis. Chowanadisai, W., Bauerly, K. A., Tchaparian, E., Wong, A., Cortopassi, G. A., Rucker, R. B., "Pyrroloquinoline quinone stimulates mitochondrial biogenesis through cAMP response element-binding protein phosphorylation and increased PGC-1alpha expression," *J. Biol. Chem.* 285(1):142-52 (2010). The only other known methods proven to stimulate mitochondrial biogenesis in aging humans are intense aerobic exercise, strict caloric restriction, and certain medications such as thiazolidinediones and the diabetes drug metformin. Lanza, IR; Sreekumaran Nair, K. "Regulation of skeletal muscle mitochondrial function: genes to proteins," *Acta Physiologica* 199(4):529-47 (2010); Spindler, S. R. "Caloric restriction: from soup to nuts," *Ageing Res. Rev.* 9 (3): 324-53 (2010); Suwa, M.; Egashira, T.; Nakano, H.; Sasaki, H.; Kumagai, S., "Metformin increases the PGC-1alpha protein and oxidative enzyme activities possibly via AMPK phosphorylation in skeletal muscle in vivo," *J. Appl. Physiol.* 101 (6): 1685-92 (2006).

Mitochondria are the primary engines of almost all bio-energy production in the human body and are among the most vulnerable physiological structures to destruction from oxidative damage. Mitochondrial dysfunction is a key biomarker of aging. Relative to cellular DNA, mitochondrial DNA possesses few defenses against free radical damage, and is dependent upon antioxidants for protection. See Bliznakov, E. G. "Aging, mitochondria, and coenzyme Q(10): the neglected relationship," *Biochimie* 81(81(12)): 1131-2 (1999); Linnane, A. W.; Marzuki, S.; Ozawa, T.; Tanaka, M. "Mitochondrial DNA mutations as an important contributor to ageing and degenerative diseases," *Lancet* 1 (8639): 642-5 (1989); Lanza, I. R.; Nair, K. S. "Mitochondrial metabolic function assessed in vivo and in vitro," *Curr. Op. Clin. Nutr. Metabol. Care* 13(5):511-7 (2010); Mota, M. P.; Peixoto, F. M.; Soares, J. F.; Figueiredo, P. A.; Leitdo, J. C.; Gaivao, I.; Duarte, J. A., "Influence of aerobic fitness on age-related lymphocyte DNA damage in humans: relationship with mitochondria respiratory chain and hydrogen peroxide production," *Age* 32 (3):337-46 (2010); Tranah, G. J. "Mitochondrial-nuclear epistasis: Implications for human aging and longevity," *Ageing Res. Rev.* 10 (2): 238-52 (2011); Cho, D H; Nakamura, T; Lipton, S. A., "Mitochondrial dynamics in cell death and neurodegeneration," *Cellular and Molecular Life Sciences* 67(20):3435-47 (2010); Richter, C. "Oxidative damage to mitochondrial DNA and its relationship to ageing," *Int'l J. Biochem. Cell Biol.* 27 (7): 647-53 (1995); Miguel, J., "An update on the mitochondrial-DNA mutation hypothesis of cell aging," *Mutation Res.* 275 (3-6): 209-16 (1992).

Three signaling molecules are reported to be activated by PQQ that cause cells to undergo spontaneous mitochondrial biogenesis: PCG-1α, CREB signaling protein, and DJ-1. See Chowanadisai, W., Bauerly, K. A., Tchaparian, E., Wong, A., Cortopassi, G. A., Rucker, R. B., "Pyrroloquinoline quinone stimulates mitochondrial biogenesis through cAMP response element-binding protein phosphorylation and increased PGC-1alpha expression," *J. Biol. Chem.* 285 (1): 142-52 (2010). PCG-1α (i.e., peroxisome proliferator-activated receptor gamma coactivator 1-alpha) is a "master regulator" that mobilizes cells' response to various external triggers. It directly stimulates genes that enhance mitochondrial and cellular respiration, growth, and reproduction. Its capacity to upregulate cellular metabolism at the genetic level favorably affects blood pressure, cholesterol and triglyceride breakdown, and the onset of obesity. The cAMP-response element-binding (CREB) signaling protein plays a pivotal role in embryonic development and growth, beneficially interacts with histones, molecular compounds shown to protect and repair cellular DNA, and stimulates the growth of new mitochondria. DJ-1 is a recently discovered cell signaling protein that, like PCG-1α and CREB, is intrinsically involved in cell function and survival and has been shown to prevent cell death by combating intensive antioxidant stress. Mitsumoto, A., Nakagawa, Y., "DJ-1 is an indicator for endogenous reactive oxygen species elicited by endotoxin," *Free Radical Res.* 35(6):885-93 (2001); Taira, T., Saito, Y., Niki, T., Iguchi-Ariga, S. M. M., Takahashi, K., Ariga, H., "DJ-1 has a role in antioxidative stress to prevent cell death," *EMBO Reports*(2): 213-8 (2004). DJ-1 is of particular importance to brain health and function. DJ-1 damage and mutation have been conclusively linked to the onset of Parkinson's disease and other neurological disorders.

PQQ is currently sold as a dietary supplement. See, e.g., Life Extension® brand PQQ Caps with BioPQQ™ capsules containing pyrroloquinoline quinone disodium salt in combination with rice flour. PQQ (and/or its salts) has been described to have cell growth promoting effects (JP Patent Publication No. 61-58584 A (1986), dermal fibroblast promoting effects, collagen elastin fibril producing effects, respiratory ability of dermal cells and Krebs cycle activating effects (EP0256472), and anti-allergic effects (JP Patent Publication No. 63-174931 A (1988)). PQQ esters have been described to have active oxygen removing effects (JP Patent Publication No. 5-078247 A (1993)), melanin production inhibitory and skin whitening effects (JP Patent Publication No. 8-020512 A (1996)), ultraviolet absorbing effects (JP Patent No. 3625493), and anti-psoriasis effects (US Patent Application Publication NO. 2010/0261749 A1).

SUMMARY OF THE INVENTION

Applicants have now discovered that topical compositions comprising PQQ esters desirably in combination with superoxide dismutase, catalase and/or catalase promoter, or a combination thereof, are effective in combating intrinsic aging from metabolism and treating skin changes, while improving skin tolerance.

Thus, the present invention is directed to topical anti-aging compositions containing PQQ esters, and their use to treat and/or prevent damage to skin caused by oxidative and degenerative processes. The compositions of the invention desirably include other components, such as superoxide dismutase, catalase and/or catalase promoter, or a combination thereof Optionally the compositions of the invention further comprise additional antioxidants.

In one embodiment, the invention is a composition comprising a PQQ ester compound of Formula I:

and salts thereof, wherein $R_1$, $R_2$, and $R_3$ simultaneously or separately represent hydrogen, a lower $C_{1-6}$ alkyl, lower $C_{2-6}$ alkenyl, lower $C_{2-6}$ alkynyl, $C_{4-12}$-aryl, $C_{4-12}$-ar-$C_{1-6}$-alkyl, or $C_{4-12}$-ar-$C_{4-12}$-aryl group. Preferably at least one of $R_1$, $R_2$, and $R_3$ is not hydrogen. In particularly preferred embodiments, the composition further comprises superoxide dismutase, catalase and/or catalase promoter, or a combination thereof.

DETAILED DESCRIPTION

In an embodiment, the invention is a composition comprising the mono-allyl ester of PQQ shown below:

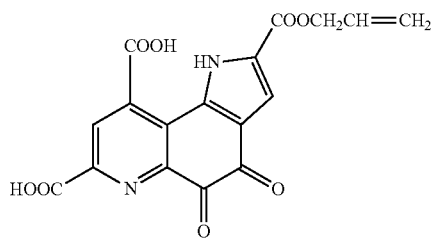

optionally in combination with superoxide dismutase and/or catalase or a catalase promoter.

The invention is further directed to a novel method of synthesizing monoesters of PQQ, wherein $R_1$ is a lower $C_{1-6}$ alkyl, lower $C_{2-6}$ alkenyl, lower $C_{2-6}$ alkynyl, $C_{4-12}$-aryl, $C_{4-12}$-ar-$C_{1-6}$-alkyl, or $C_{4-12}$-ar-$C_{4-12}$-aryl group. The method generally involves formation of an arylhydrazone by reaction with the appropriate 2-methylacetoacetate ester. In preferred embodiments, the novel synthetic method is used to prepare the mono-allyl ester of PQQ shown above comprising the step of forming an arylhydrazone by reaction with allyl 2-methylacetoacetate.

The compositions of the invention can be used to treat or prevent a wide variety of skin changes. Skin changes that can be treated or prevented include, inter alia, erythematous; inflammatory, allergic or autoimmune-reactive symptoms, in particular dermatoses; skin changes in light-sensitive skin, particularly photodermatoses; and damaging effects of the UV part of solar radiation on the skin. Thus the invention is also directed to a method of treating or preventing the worsening of a skin change including treating or preventing skin aging (e.g., wrinkling, fine lines), hyperpigmentation (e.g., age spots), UV damage, photodamage, photoreactions, inflammatory symptoms and skin conditions such as erythematous, cellulitis, rosacea, acne, eczema, dermatitis (atopic or contact), and pruritis, comprising topically administering a therapeutically effective amount of a compound of Formula I, alone or in combination with superoxide dismutase and/or catalase or catalase promoter to a patient in need thereof Compositions of the present invention can be used to reduce, if not completely prevent, damage to the skin caused by oxidative influence, and cause a regenerating and vitalizing effect on aging, stressed, or damaged skin by supporting vesicular breathing, stabilization of mitochondrial membranes, and anti-apoptotic properties. Compositions of the present invention can also be used to promote growth of dermal fibroblasts and growth of extracellular matrix molecules in skin, including the promotion of the growth of fibril proteins such as collagen, elastin, and keratin, microfibrillar associated glycoproteins such as MAGP-1 and MAGP-2, glycosaminoglycans (GAGs) such as hyaluronic acid, dermatan sulfate, chondroitin sulfate, heparin, heparan sulfate, keratan sulfate and their derivatives, proteoglycans, and combinations thereof In addition, the compositions of the invention can be used to promote skin changes that improve the appearance of skin, including skin tightening, skin brightening, skin illuminating, skin smoothing, skin moistening, skin plumping, skin firming, evening of skin tone, reducing skin redness, minimizing the appearance of dark circles, improving skin elasticity and recoilability, improving overall skin cell health, reducing pore size, and reducing the appearance of fine lines, wrinkles and skin blemishes resulting from acne or aging. Thus, the invention is also directed to a method of improving the appearance of skin comprising topically administering a therapeutically effective amount of a compound of Formula I, alone or in combination with superoxide dismutase and/or catalase or catalase promoter to a patient in need thereof.

The present invention pertains to cosmetic and/or dermatological compositions comprising PQQ, its esters, or salts thereof, that promote skin changes that improve skin health or appearance, e.g., by providing the dermal cells a friendly environment in which to undergo natural skin repair processes. In addition, or alternatively, the present invention pertains to cosmetic and/or dermatological compositions comprising PQQ, its esters, or salts thereof, that reduce skin changes that result in unhealthy or unattractive skin, e.g., by preventing damage to lipids, DNA, and proteins, or by protecting the skin against photo-reactions and/or inflammatory reactions. The compositions of the present invention provide a significantly improved antioxidant effectiveness (Environmental Protection Factor® (EPF)) compared to other compositions comprising PQQ or its esters. The compositions of the present invention also exhibit greater stability than other PQQ-containing skin care compositions and less skin irritation or inflammation than other PQQ-containing skin care compositions.

In particular, the present invention pertains to cosmetic and/or dermatological compositions comprising a compound of Formula I:

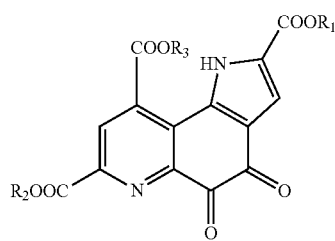

and salts thereof $R_1$, $R_2$, and $R_3$ simultaneously or separately represent hydrogen, a lower alkyl, lower alkenyl, lower alkynyl, aryl, aralkyl, or araryl group. Desirably the lower alkyl group is a $C_{1-10}$ alkyl, more preferably a $C_{1-6}$ alkyl. For example, the alkyl group can be methyl, ethyl, n-propyl, i-propyl, n-butyl, t-butyl, s-butyl, pentyl, etc. Desirably the lower alkenyl group is a $C_{2-10}$, more preferably a $C_{2-6}$ alkenyl group. For example, the alkenyl group can be allyl, 2-butenyl, 1,3-butadienyl, etc. Desirably the lower alkynyl group is a $C_{2-10}$, more preferably a $C_{2-6}$ alkynyl group. Desirably the aryl group is a substituted or unsubstituted $C_{4-10}$ aryl group. For example the aryl group can be phenyl. Desirably the aralkyl group contains a $C_{4-10}$ aryl group and a $C_{1-4}$ alkyl. For example, the aralkyl group can be methylphenyl, ethylphenyl, etc. The aryl group can be benzyl, methylbenzyl, etc.

Desirably at least one of $R_1$, $R_2$, and $R_3$ is not hydrogen. Preferred compounds of Formula I include the trimethyl ester, dimethyl ester, monomethyl ester, triethyl ester, diethyl ester, monoethyl ester, triaryl ester, diallyl ester, monoallyl ester, tribenzyl ester, dibenzyl ester, monobenzyl ester, trimethylphenyl ester, dimethylphenyl ester, and monomethylphenyl ester.

In some preferred embodiments, at least one of $R_1$, $R_2$, and $R_3$ is an alkenyl group, more preferably an allyl group, while the remaining two groups are hydrogen or a lower alkyl. In even more preferred embodiments, $R_1$ is allyl and $R_2$ and $R_3$ are hydrogen such that the compound has the chemical structure shown below.

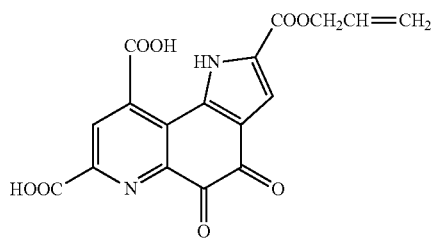

The compounds of Formula I can be synthesized from PQQ by any suitable means, including those methods described in JP 08-020512. Generally such compounds can be prepared by esterification of PQQ. Partial hydrolysis of triesters be carried out to yield diesters and monoesters of PQQ. For example, trisallylation can be carried out by heating PQQ in the presence of an allyl halide (e.g., allyl bromide, allyl iodide, allyl chloride) and reacting with base (e.g., any of the lithium, potassium, sodium or cesium salts of carbonate or hydroxide) followed by selective base hydrolysis (e.g., using any of the same bases) in water or in a mixture of water with an organic solvent (e.g., acetonitrile, THF, dioxane, methanol, ethanol, propanol) to obtain the monoallyl ester shown above. Purification can be carried out using conventional column chromatographic means.

Alternatively compounds of Formula I, especially those wherein $R_1$, $R_2$, and/or $R_3$ are selected from hydrogen, lower alkyl (e.g., methyl, ethyl, propyl, isopropyl, butyl, isobutyl), lower alkenyl (e.g., vinyl, allyl, 2-butenyl, 3-methyl-2-butenyl, 2-pentenyl, 3-methyl-2-pentenyl, 3-ethyl-2-pentenyl), lower alkynyl (e.g., ethynyl, propynyl, butynyl, 2-butynyl), and aryl (phenyl or substituted phenyl such as tolyl) are synthesized by a novel method involving formation of an arylhydrazone by reaction with a 2-methylacetoacetate ester. For example, the novel synthetic method can be used to prepare the mono-allyl ester of PQQ shown above comprising the step of forming an arylhydrazone by reaction with allyl 2-methylacetoacetate.

In particular, the method involves (i) protecting the aniline group and reducing the nitro group of 2-methoxy-5-nitroaniline, (ii) converting the resulting compound to a diazonium salt followed by a Japp-Klingemann type reaction with an appropriate 2-methylacetoacetate ester (e.g., allyl 2-methylacetoacetate) to afford an arylhydrazone, (iii) converting the arylhydrazone to an indole via a Fisher indole reaction by heating in acid, (iv) deprotecting the aniline nitrogen, (v) reacting with an appropriate keto ester (e.g., dimethyl 2-oxoglutaconate) to produce a triester (e.g., 2-allyl-7,9-dimethyl pyrroloquinoline triester), (vi) oxidizing, and optionally (vii) selectively hydrolyzing the $R_2$ and $R_3$ esters to yield the desired ester of PQQ (e.g., the mono-allyl ester of PQQ shown above).

A general reaction scheme is shown below:

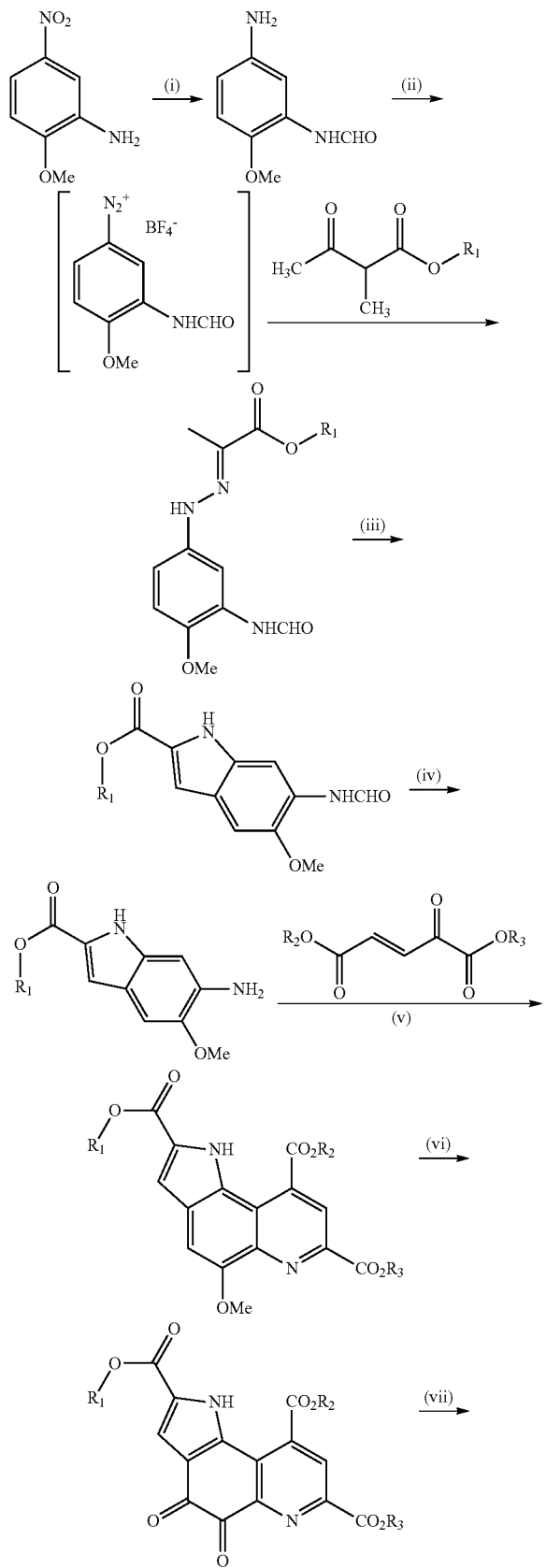

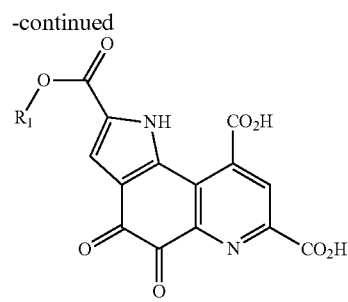

Suitable solvents, reagents and reaction conditions for carrying out the above general reaction scheme are known in the art and the selection of the particular solvents, reagents and reaction conditions is within the skill of the person of ordinary skill in the art.

Preferably step (i) is carried out by reaction of commercially available 2-methoxy-5-nitroaniline with formic acid in the presence of acetic anhydride and water, followed by hydrogenation using Pt or Pd (C) catalyst and hydrogen gas in an organic solvent (e.g., DMF, methanol, ethanol, or isopropanol).

Preferably step (ii) is carried out by reacting the product of step (i) with concentrated hydrochloric acid or any suitable mineral acid, sodium nitrite and fluoroboric acid in the presence of water and ethanol to form a diazonium salt which is then reacted with an appropriate 2-alkyl acetoacetate ester and base (e.g., sodium acetate, sodium hydroxide, potassium hydroxide) to afford an arylhydrazone.

Preferably step (iii) is a Fisher Indole reaction, which requires heating the product of step (ii) with a suitable acid, many of which are known in the art, to produce an indole. Preferred acids include formic acid, sulfuric acid, polyphosphoric acid, p-toluene sulfonic acid, and the like.

Preferably step (iv) is carried out by reaction of the product of step (iii) with hydrochloric acid in an organic solvent (e.g., acetone, methanol, ethanol, isopropanol, dioxane) followed by neutralization with base (e.g., NaOH, KOH, LiOH, $K_3PO_4$, $K_2HPO_4$, $KH_2PO_4$).

Preferably step (v) is carried out by reacting the product of step (iv) via a Doebner-Miller quinoline reaction with an appropriate keto ester (e.g., dimethyl 2-oxoglutaconate) in organic solvent, preferably halogenated organic solvent (e.g., dichloromethane, dichloroethane, chloroform), followed by a dehydration/oxidation reaction using hydrogen chloride (e.g., concentrated or as in organic solvent such as acetone, dioxane, methanol, ethanol, isopropanol) in the presence of oxygen, optionally in the presence of copper acetate, to produce a triester (e.g., 2-allyl-7,9-dimethyl pyrroloquinoline triester).

Preferably step (vi) is carried out by reaction of the product of step (v) with cerium ammonium nitrate or cerium ammonium sulfate, in aqueous/organic solvent mixtures (e.g., aqueous acetonitrile).

Finally, step (vii) (if desired) is preferably carried out by reacting the product of step (vi) with a suitable selective hydrolysis agent (e.g., LiOH, NaOH, KOH, trifluoroacetic acid (TFA), or a carbonate or bicarbonate salt such as potassium carbonate, sodium carbonate, potassium bicarbonate, or sodium bicarbonate) in water or a mixture of water and organic solvent (e.g., methanol, ethanol, isopropanol, THF, dioxane, $CH_3CN$) to selectively hydrolyze the $R_2$ and/or $R_3$ esters to yield the desired mono- or di-ester of PQQ.

Desirably the mono-allyl ester of PQQ (1) is prepared by the reaction scheme shown below.

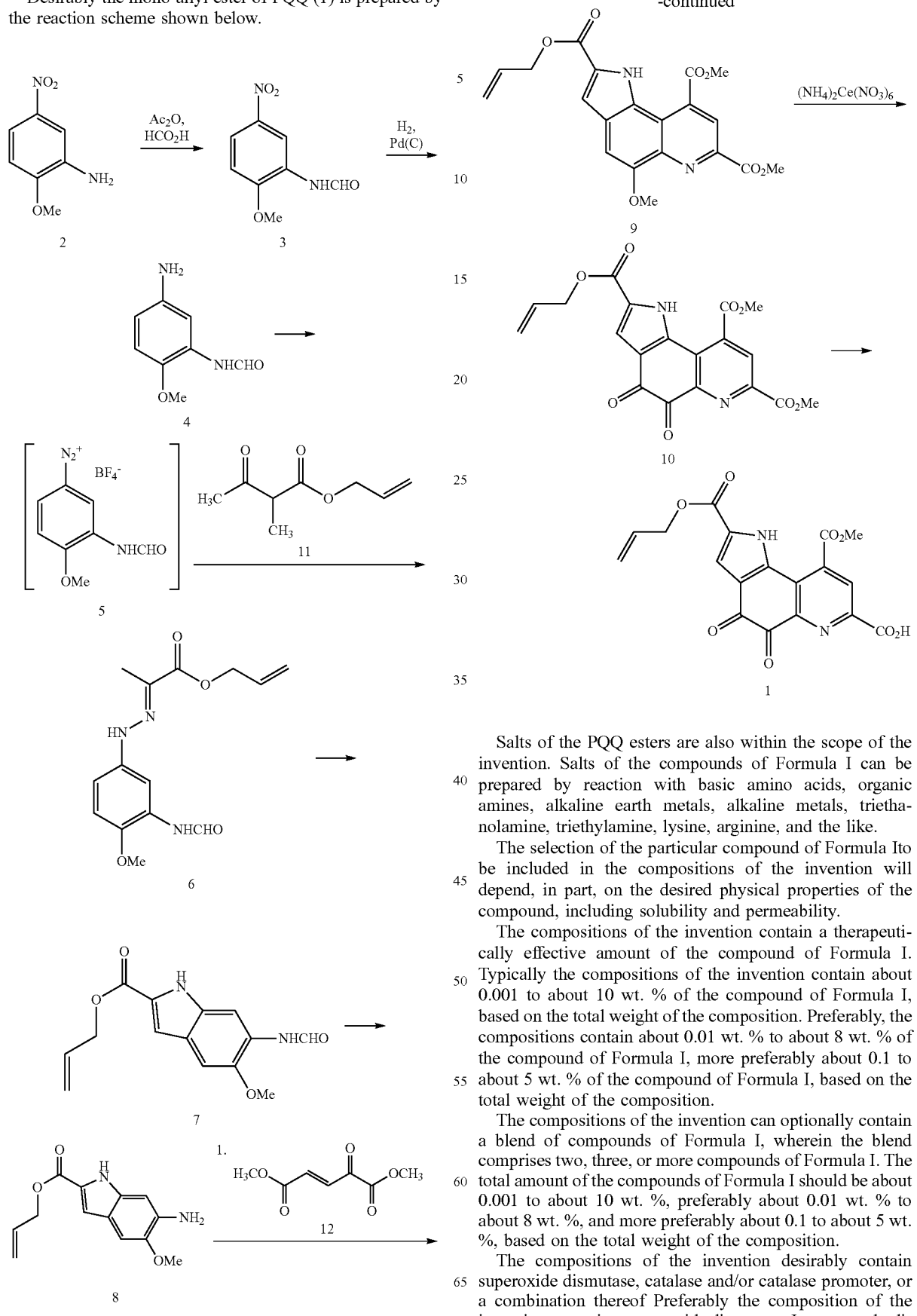

Salts of the PQQ esters are also within the scope of the invention. Salts of the compounds of Formula I can be prepared by reaction with basic amino acids, organic amines, alkaline earth metals, alkaline metals, triethanolamine, triethylamine, lysine, arginine, and the like.

The selection of the particular compound of Formula I to be included in the compositions of the invention will depend, in part, on the desired physical properties of the compound, including solubility and permeability.

The compositions of the invention contain a therapeutically effective amount of the compound of Formula I. Typically the compositions of the invention contain about 0.001 to about 10 wt. % of the compound of Formula I, based on the total weight of the composition. Preferably, the compositions contain about 0.01 wt. % to about 8 wt. % of the compound of Formula I, more preferably about 0.1 to about 5 wt. % of the compound of Formula I, based on the total weight of the composition.

The compositions of the invention can optionally contain a blend of compounds of Formula I, wherein the blend comprises two, three, or more compounds of Formula I. The total amount of the compounds of Formula I should be about 0.001 to about 10 wt. %, preferably about 0.01 wt. % to about 8 wt. %, and more preferably about 0.1 to about 5 wt. %, based on the total weight of the composition.

The compositions of the invention desirably contain superoxide dismutase, catalase and/or catalase promoter, or a combination thereof Preferably the composition of the invention comprises superoxide dismutase. In some embodiments, the composition of the invention comprises superoxide dismutase and catalase. In other embodiments, the composition of the invention comprises superoxide dismutase and catalase promoter. In yet other embodiments, the composition of the invention comprises superoxide dismutase, catalase and catalase promoter.

Superoxide dismutase (SOD) is an enzyme that catalyzes the dismutation of superoxide into oxygen and hydrogen peroxide. Desirably the SOD has a molecular weight between 10,000 and 30,000. The amount of SOD present in the composition desirably is about 0.0001 to about 1 wt. %, based on the total weight of the composition. Preferably the amount of SOD is about 0.001 wt. % to about 0.05 wt. %, based on the total weight of the composition.

Catalase is an enzyme that functions to catalyze the decomposition of hydrogen peroxide to water and oxygen. The catalase can be from any suitable source, for example a bovine source, a bacterial source or a fungal source. Preferably the catalase is from a bacterial or fungal source. The amount of catalase present in the composition desirably is about 0.000001 to about 0.1 wt. %, based on the total weight of the composition. Preferably the amount of catalase is about 0.00001 wt. % to about 0.01 wt. %, based on the total weight of the composition.

Catalase promoter is a compound or extract that induces endogenous catalase formation. Suitable compounds include botanicals such as bacopa monniera, silybum marianum (milk thistle), withania somnifera (ashwagandha), camellia sinensis (green tea), curcuma longa (turmeric), centella asiatica, gingko biloba, N-acetyl cysteine, and mixtures thereof See U.S. Pat. No. 7,241,461. The amount of catalase promoter present in the composition desirably is about 0.001 wt. % to about 2 wt. %, based on the total weight of the composition. Preferably the amount of catalase promoter is about 0.01 wt. % to about 1 wt. %, based on the total weight of the composition.

The compositions of the present invention typically contain at least one additive. Suitable additives include, but are not limited to, surfactants, cosmetic auxiliaries, pigments, UVA filters, UVB filters, skin absorption promoting agents, propellants, thickening agents, emulsifiers, solvents (e.g., alcoholic solvents), water, antioxidants, perfumes, dyestuffs, deodorants, antimicrobial materials, back-fatting agents, complexing and sequestering agents, exfoliating agents, pearlescent agents, plant extracts, vitamins, active ingredients, and/or derivatives and combinations thereof.

The compositions of the invention optionally further comprise substances which absorb UV radiation in the UVB range, wherein the total quantity of filter substances is, for example 0.1 wt % to 30 wt %, preferably 0.5 to 10 wt %, more preferably 1.0 to 6.0 wt %, based on the total weight of the compositions, in order to provide cosmetic compositions which protect the skin from the entire range of ultraviolet radiation and serve as sunscreen agents for the skin. Suitable UVB filter substances include oil-soluble and water-soluble substances. Advantageous oil-soluble UVB filters include, for example, mineral oils, mineral waxes, oils such as triglycerides of capric or caprylic acid, natural oils such as castor oil, fats, waxes and other natural and synthetic adipoids, preferably esters of fatty acids with alcohols of low C number, for example with isopropanol, propylene glycol or glycerine, or esters of fatty alcohols with alkane acids of low C number or with fatty acids; alkyl benzoates; silicone oils, such as dimethylpolysiloxanes, diethylpolysiloxanes, diphenylpolysiloxanes and mixtures thereof 3-Benzylidene camphor derivatives, preferably 3-(4-methylbenzylidene) camphor, 3-benzylidene camphor; 4-aminobenzoic acid derivatives, preferably (2-ethylhexyl) 4-(dimethylamino) benzoate, amyl 4-(dimethylamino) benzoate; esters of cinnamic acid, preferably (2-ethylhexyl) 4-methoxycinnamate, isopentyl 4-methoxycinnamate; esters of salicylic acid, preferably (2-ethylhexyl) salicylate, (4-isopropyl-benzyl) salicylate, homomentyl salicylate, derivatives of benzophenone, preferably 2-hydroxy-4-methoxybenzophenone, 2-hydroxy-4-methoxy-4'-methylbenzophenone, 2,2'-dihydroxy-4-methoxybenzophenone; esters of benzylidenemalonic acid, preferably di(2-ethylhexyl) 4-methoxybenzylidenemalonate, 2,4,6-trianilino(p-carbo-2'-ethyl-1'-hexyloxy)-1,3,5-triazine.

Advantageous water-soluble UVB filters include salts of 2-phenylbenzimidazole-5-sulphonic acid (e.g., sodium, potassium or triethanolammonium salts), sulfonic acid and sulfonic acid derivatives of benzophenones, preferably 2-hydroxy-4-methoxy benzophenone-5-sulphonic acid and their salts; sulfonic acid derivatives of 3-benzylidene camphor, such as for example 4-(2-oxo-3-bornylidenemethyl) benzene sulfonic acid, 2-methyl-5-(2-oxo-3-bornylidenemethyl)sulfonic acid and their salts, as well as 1,4-di(2-oxo-10-sulpho-3-bornylidene-methyl)benzene and its salts (the corresponding 10-sulfato compounds, for example the corresponding sodium, potassium or triethanolammonium salt), also designated as benzene-1,4-di(2-oxo-1-bornylidene-methyl)-10-sulfonic acid.

The compositions of the invention also optionally further comprise substances which absorb UV radiation in the UVA range, wherein the total quantity of filter substances is, for example 0.1 wt % to 30 wt %, preferably 0.5 to 10 wt %, more preferably 1.0 to 6.0 wt %, based on the total weight of the compositions, in order to provide cosmetic compositions which protect the skin from the entire range of ultraviolet radiation and serve as sunscreen agents for the skin. Suitable UVA filter substances include derivatives of dibenzoylmethane, in particular 1-(4'-tertbutylphenyl)-3-(4'-methoxyphenyl)propane-1,3-dione and 1-phenyl-3-(4'-isopropyl-phenyl)propane-1,3-dione.

The compositions of the invention can also optionally contain inorganic pigments, which are used conventionally in cosmetics to protect the skin from UV rays. Suitable inorganic pigments include oxides of titanium, zinc, zirconium, silicon, iron, manganese, cerium and mixtures thereof, and modifications in which the oxides are the active agents. Preferably the inorganic pigments are based on titanium dioxide.

In some embodiments, the compositions of the invention comprise both a UVB filter substance and a UVA filter substance. In other embodiments, the compositions comprise a UVB filter and an inorganic pigment or a UVA filter substance and an inorganic pigment. In yet other embodiments, the compositions of the invention comprise a UVB filter substance, a UVA filter substance, and an inorganic pigment.

In other preferred embodiments, the composition further comprises a skin absorption promoting agent. The absorption promoting agents are substances capable of improving the diffusion of active ingredients in the epidermis, in particular the stratum corneum. These adjuvants can be classified in different families according to their chemical structure. Suitable skin absorption promoting agents are known in the art. As an example of absorption promoting agents, dioxolane derivatives such as isopropylidene glycerol, marketed under the name Solketal or 2n-nonyl 1-3 dioxolane; or diethylene glycol monoethyl ether (for example that marketed under the tradename Transcutol®) can in particular be mentioned. Absorption promoting agents are also described in the following chemical families: polyols, fatty acids, esters of fatty acids alcohols and amides. As an example of substances representative of these families, propylene glycol monocaprylate or Capryol 90, caprylic acid, diisopropyl adipate, polysorbate 80, 2-octyl dodecanol and 1-dodecylazacyclohepta-2-one or Azone, can in particular be mentioned. Substances presenting properties of absorption promoting agents can also be found in the family of sulfoxides (such as for example dimethylsulfoxide), terpenes (for example d-limonene), alkanes (for example N-heptane) or organic acids (for example alpha hydroxy acids such as glycolic acid and lactic acid, and salts thereof, or salicylic acid and salicylates). The quantity of absorption promoting agent in the compositions according to the invention, varies from 2 to 12% by weight of the total composition.

In some embodiments of the invention, the composition further comprises additional antioxidants and/or free radical absorbers. A variety of suitable antioxidants which are suitable or conventional for cosmetic and/or dermatological applications are known in the art and can be used according to the invention as favorable antioxidants. For example, suitable antioxidants include resveratrol, amino acids (e.g., glycine, histidine, tyrosine, tryptophan) and their derivatives, imidazoles (e.g., urocanic acid) and their derivatives, peptides (e.g., D,L-carnosine, D-carnosine, L-carnosine) and their derivatives (e.g., anserine), carotinoids, carotenes (e.g., alpha-carotene, beta-carotene, lycopene) and their derivatives, chlorogenic acid and its derivatives, lipoic acid and its derivatives (e.g., dihydrolipoic acid), aurothioglucose, propylthiouracil and other thiols (e.g., thioredoxin, glutathione, cysteine, cystine, cystamine and their glycosyl, N-acetyl, methyl, ethyl, propyl, amyl, butyl and lauryl, palmitoyl, oleyl, gamma-linoleyl, cholesteryl and glyceryl esters) and their salts, dilauryl thiodipropionate, distearyl thiodipropionate, thiodipropionic acid and their derivatives (esters, ethers, peptides, lipids, nucleotides, nucleosides and salts) and sulphoximine compounds (e.g., buthionine sulphoximines, homocysteine sulphoximine, buthionine sulfones, pentathionine sulphoximine, hexathionine sulphoximine, heptathionine sulphoximine) in very low, acceptable doses (e.g., pmole to pmoles/kg), also (metal) chelating agents (e.g., alpha-hydroxy fatty acids, palmitic acid, phytic acid, lactoferrin), alpha-hydroxy acids (e.g., citric acid, lactic acid, malic acid, mandelic acid), humic acid, colic acid, colic extracts, bilirubin, biliverdin, EDTA, EGTA and their derivatives, unsaturated fatty acids and their derivatives (e.g., gamma-linolenic acid, linolic acid, oleic acid), folic acid and their derivatives, ubiquinone and ubiquinol and their derivatives, vitamin C and derivatives (e.g., ascorbyl palmitate, Mg-ascorbyl phosphate, ascorbyl acetate), tocopherols and derivatives (e.g., vitamin E acetate), vitamin A and derivatives (e.g., vitamin A palmitate) and coniferyl benzoate of benzoin resin, rutinic acid and their derivatives, butylhydroxy toluene, butylhydroxy anisole, nordihydroguaiacic acid, nordihydroguaiaretic acid, trihydroxybutyrophenone, uric acid and its derivatives, mannose and its derivatives, sesamol, sesamolin, zinc and its derivatives (e.g., ZnO, ZnSO$_4$), selenium and its derivatives (e.g., selenium methionine), and stilbenes and their derivatives (e.g., stilbene oxide, trans-stilbene oxide, resveratrol), wherein suitable derivatives include salts, esters, ethers, sugars, nucleotides, nucleosides, peptides and lipids of these said active ingredients.

The quantity of the aforementioned antioxidants (one or more compounds) in the compositions can be 0.0001 wt % to 30 wt %, preferably 0.05 wt % to 20 wt %, more preferably 1-10 wt %, based on the total weight of the composition.

The cosmetic and dermatological compositions of the invention optionally further comprise one or more cosmetic auxiliaries, as are used conventionally in such compositions, for example preservatives, bactericides, perfumes, substances for preventing foaming, dyestuffs, pigments which have a coloring effect, thickening agents, surfactant substances, emulsifiers, softening, moisturizing and/or moisture-retaining substances, exfoliating agents, fats, oils, waxes or other conventional constituents of a cosmetic or dermatological formulation, such as alcohols, polyols, polymers, foam stabilizers, electrolytes, organic solvents or silicone derivatives.

The composition of the invention desirably has an improved antioxidant effectiveness (e.g., Environmental Protection Factor® (EPF) factor) compared to prior art compositions, including prior art compositions comprising PQQ or its esters. Environmental Protection Factor® (EPF) antioxidant effectiveness is a standard of measuring the power of antioxidants, based on a series of tests, for example two or more tests including, for example, sun burn cell assay, photochemilluminescence, primary oxidative products, secondary oxidative products, and UVB irradiated keratinocytes. A method for evaluating the antioxidant effectiveness (EPF®) of an antioxidant is described in U.S. patent application Ser. No. 11/050,571, which is incorporated by reference herein. The power of each antioxidant is evaluated on a 100-point scale, with each test having a maximum of 20 points. The antioxidant effectiveness of the compositions of the invention depends, in part, on the antioxidant effectiveness of the individual antioxidants present in the composition. Compositions of the invention having improved antioxidant effectiveness can be obtained by including the compound of Formula I alone or in combination with other antioxidants so as to obtain a composition having an antioxidant effectiveness value (EPF® value) approaching 100 (e.g., a value of 90 or more, 93 or more, 95 or more, 97 or more, 99 or more, or even 100). It is believed that compositions comprising the compound of Formula I in combination with superoxide dismutase and/or catalase or catalase promoter, optionally in combination with other antioxidants, have a synergistically improved antioxidant effectiveness compared to compositions containing the components individually.

The cosmetic or dermatological compositions of the invention can be conventionally prepared and then used to provide treatment, care, and cleansing of the skin, and as a make-up product in decorative cosmetics, for example, as dry powder formulations of minerals, natural minerals and earth-derived pigments. For administration, the PQQ esters can be topically applied to the skin in cosmetic and dermatological compositions of the invention in the manner conventional for cosmetics.

Cosmetic and dermatological compositions of the invention can exist in various forms. For example, the compositions of the invention can be in the form of a cream, a solution, a serum, an anhydrous preparation, an emulsion or microemulsion of the type water-in-oil (W/O) or of the type oil-in-water (O/W), a multiple emulsion, for example of the type water-in-oil-in-water (W/O/W), a gel, a solid stick, an ointment or an aerosol. It is also advantageous to administer PQQ esters in encapsulated form, for example in collagen matrices and other conventional encapsulation materials, for example as cellulose encapsulations, in gelatin, in wax matrices or as liposomal encapsulations. Preferably the composition of the invention is in the form of a cream. It is also possible and advantageous within the scope of the present invention to add PQQ esters to aqueous systems or surfactant compositions for cleansing the skin.

Emulsions according to the present invention are advantageous and contain, for example, the afore-mentioned fats, oils, waxes and other adipoids, and water and an emulsifier, as is used conventionally for such a type of formulation.

The lipid phase can advantageously be selected from the following substance group: mineral oils, mineral waxes; oils, such as triglycerides of capric or caprylic acid, also natural oils, such as for example castor oil; fats, waxes and other natural and synthetic adipoids, preferably esters of fatty acids with alcohols of low C number, for example with isopropanol, propylene glycol or glycerine, or esters of fatty alcohols with alkane acids of low C number or with fatty acids; alkyl benzoates; silicone oils, such as dimethylpolysiloxanes, diethylpolysiloxanes, diphenylpolysiloxanes and mixtures thereof The oil phase of the emulsions, oleogels or hydrodispersions or lipodispersions within the scope of the present invention is advantageously selected from the group of esters of saturated and/or unsaturated, branched and/or unbranched alkane carboxylic acids of chain length from 3 to 30 C atoms and saturated and/or unsaturated, branched and/or unbranched alcohols of chain length from 3 to 30 C atoms, from the group of esters from aromatic carboxylic acids and saturated and/or unsaturated, branched and/or unbranched alcohols of chain length from 3 to 30 C atoms. Such ester oils can then advantageously be selected from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic, and natural mixtures of such esters, for example jojoba oil.

Furthermore, the oil phase can advantageously be selected from the group of branched and unbranched hydrocarbons and waxes, silicone oils, dialkyl ethers, the group of saturated or unsaturated, branched or unbranched alcohols, and fatty acid triglycerides, namely the triglycerine esters of saturated and/or unsaturated, branched and/or unbranched alkane carboxylic acids of chain length from 8 to 24, in particular 12-18, C atoms. The fatty acid triglycerides can advantageously be selected, for example from the group of synthetic, semi-synthetic and natural oils, for example olive oil, sunflower oil, soybean oil, peanut oil, rape-seed oil, almond oil, palm oil, coconut oil, palm kernel oil and the like.

Also any mixtures of such oil and wax components can be used advantageously within the scope of the present invention. It can also optionally be advantageous to use waxes, for example cetyl palmitate, as the single lipid component of the oil phase.

The oil phase is advantageously selected from the group 2-ethylhexyl isostearate, octyl-5-dodecanol, isotridecyl isononanoate, isoeicosane, 2-ethylhexyl cocoate, $C_{12-15}$ alkyl benzoate, capryl-capric acid triglyceride, dicaprylyl ether.

Mixtures of $C_{12-15}$ alkyl benzoate and 2-ethylhexyl isostearate, mixtures of $C_{12-15}$ alkyl benzoate and isotridecyl isononanoate and mixtures of $C_{12-15}$ alkyl benzoate, 2-ethylhexyl isostearate and isotridecyl isononanoate are particularly advantageous.

Of the hydrocarbons, paraffin oil, squalane and squalene can be used advantageously within the scope of the present invention.

The oil phase can advantageously also contain cyclic or linear silicone oils or can consist completely of such oils, but wherein it is preferable, apart from the silicone oil or the silicone oils, to use an additional amount of other oil phase components.

Cyclomethicone (octamethylcyclotetrasiloxane) is advantageously employed as silicone oil to be used according to the invention. However, other silicone oils should also advantageously be used within the scope of the present invention, for example hexamethylcyclotrisiloxane, polydimethylsiloxane, poly(methylphenylsiloxane). Mixtures of cyclomethicone and isotridecyl isononanoate, of cyclomethicone and 2-20 ethylhexyl isostearate, are also particularly advantageous.

The aqueous phase of the compositions of the invention can optionally contain advantageously alcohols, diols or polyols of low C number, and their ethers, preferably ethanol, isopropanol, propylene glycol, glycerine, ethylene glycol, ethylene glycol monoethyl or monobutyl ether, propylene glycol monomethyl, monoethyl or monobutyl ether, diethylene glycol monomethyl or monoethyl ether and analogous products, also alcohols of low C number, for example ethanol, isopropanol, 1,2-propane diol, glycerine and, in particular, one or more thickening agents, which can advantageously be selected from the group silicon dioxide, aluminum silicates, polysaccharides or their derivatives, for example hyaluronic acid, xanthan gum, hydroxypropylmethylcellulose, particularly advantageously from the group of polyacrylates, in each case individually or in combination.

Mixtures of the above-mentioned solvents are used in particular. For alcoholic solvents, water can be a further constituent.

Gels according to the present invention conventionally contain alcohols of low C number, for example ethanol, isopropanol, 1,2-propane diol, glycerine and water or an above-mentioned oil in the presence of a thickening agent, which for oily-alcoholic gels is preferably silicon dioxide or an aluminum silicate, for aqueous-alcoholic or alcoholic gels is preferably a polyacrylate.

The conventionally-known, highly volatile, liquefied propellants, for example hydrocarbons (propane, butane, isobutane), which can be used alone or mixed with one another, are suitable as propellants for compositions which can be sprayed from aerosol containers according to the present invention. Compressed air can also advantageously be used.

Cosmetic compositions of the invention which are a skin-cleansing agent or shampooing agent preferably contain at least one anionic, non-ionic or amphoteric surfactant substance, or also mixtures of such substances, PQQ esters in aqueous medium and auxiliaries, as are used conventionally therefore. The surfactant substance or the mixtures of these substances can be present in the shampooing agent in a concentration between 1 wt % and 50 wt %.

These cosmetic or dermatological compositions can also be aerosols having the auxiliaries conventionally used therefor.

Aqueous cosmetic cleansing agents of the invention or low-water or anhydrous cleansing agent concentrates intended for aqueous cleansing can contain anionic, non-ionic and/or amphoteric surfactants, for example traditional soaps, for example fatty acid salts of sodium alkyl sulfates, alkyl ether sulfates, alkane and alkyl benzene sulfonates, sulfoacetates, sulphobetaines, sarcosinates, amidosulfobetaines, sulfosuccinates, sulfosuccinic acid semiesters, alkyl ether carboxylates, protein-fatty acid condensates, alkylbetaines and amidobetaines fatty acid alkanol amides polyglycol ether derivatives.

Compositions of the invention, which are cosmetic cleansing compositions for the skin, can be present in liquid or solid form. In addition to PQQ esters, they preferably contain at least 5 one anionic, non-ionic or amphoteric surfactant substance or mixtures thereof, if required one or more electrolytes and auxiliaries, as are used conventionally therefor. The surfactant substance can be present in the cleansing compositions in a concentration between 0.001 and 99.999 wt %, based on the total weight of the compositions.

Compositions of the invention, which are a shampooing agent, in addition to an effective amount of PQQ esters, preferably contain an anionic, non-anionic or amphoteric surfactant substance or mixture thereof, optionally an electrolyte of the invention and auxiliaries, as are used conventionally therefor. The surfactant substance can be present in the shampooing agent in a concentration between 0.001 wt % and 99.999 wt %.

The compositions of the invention contain, apart from the afore-mentioned surfactants, water and optionally the additives which are conventional in cosmetics, for example perfume, thickener, dyestuffs, deodorants, antimicrobial materials, back-fatting agents, complexing and sequestering agents, pearlescent agents, plant extracts, vitamins and/or their derivatives, active ingredients and the like.

The compositions of the invention are suitable for use in a method of reducing or eliminating damage from intrinsic skin aging due to declining metabolism comprising topically administering to a subject in need thereof. For example, the compositions of the invention can be used to slow or reverse damage from intrinsic skin aging due to metabolism including decreased collagen production, decreased elasticity of skin, decreased skin thickness, decreased cell turnover, decreased number of blood vessels in the dermis, decreased number of elastins, decreased oil and sweat production, development of benign and malignant skin tumors, and formation of age spots.

The compositions of the invention are suitable for use in a method of increasing cell life span, comprising topically administering to a subject in need thereof Pro-oxidative degradation products do not occur when using PQQ esters of Formula I. The use of PQQ esters as antioxidants and their use for combating and/or prophylaxis of skin aging caused by oxidative stress and inflammatory reactions are within the scope of the present invention. The use of PQQ esters as antioxidants for the stabilization of cosmetic or dermatological compositions, which contain as additive either vitamin A and/or its derivatives (for example, all-E-retinoic acid, 9-Z-retionoic acid, 13-Z-retinoic acid, retinal, retinyl ester), vitamin B and/or its derivatives, vitamin C and/or its derivatives and vitamin E and/or its derivatives (for example, alpha-tocopherol acetate) individually or in combination, is thus likewise within the scope of the present invention. The stabilizing effect of the present invention relates to both smell and color and in particular to the active ingredient content of the composition.

Further, the use of PQQ esters as an agent for supporting vesicular breathing and stabilization of mitochondrial membranes with additional anti-apoptotic effect in skin cells and its use for the regeneration and revitalization of aging, stressed or damaged skin, is within the scope of the present invention.

The use of PQQ for the protection of the skin from oxidative stress is also regarded as an advantageous embodiment of the present invention, in particular the use of PQQ esters in washing formulations.

The present invention also includes a cosmetic process for protecting the skin and the hair from oxidative or photooxidative processes, which is characterized in that a cosmetic agent, which contains an effective concentration of PQQ esters, is applied to the skin or hair in adequate quantity.

Likewise, the present invention also includes a process for protecting cosmetic or dermatological compositions from oxidation or photo-oxidation, wherein these compositions, for example compositions for treating and caring for the hair are, in particular hair lacquers, shampooing agents, also make-up products, such as for example nail varnishes, lipsticks, foundations, washing and showering compositions, creams for treating or caring for skin or other cosmetic compositions, the constituents of which can bring with them stability problems due to oxidation or photo-oxidation on storage, characterized in that the cosmetic compositions have an effective amount of PQQ esters.

Also within the scope of the present invention are processes for producing the cosmetic agents of the invention, which is characterized in that active ingredient combinations of the invention are incorporated into cosmetic and dermatological formulations in a manner known to one of skill in the art.

EXAMPLES

The use of these and other examples anywhere in the specification is illustrative only, and in no way limits the scope and meaning of the invention or of any exemplified form. Likewise, the invention is not limited to any particular preferred embodiments described herein. Indeed, modifications and variations of the invention can be apparent to those skilled in the art upon reading this specification, and can be made without departing from its spirit and scope. The invention is therefore to be limited only by the terms of the appended claims, along with the full scope of equivalents to which the claims are entitled.

Example 1

Synthesis of Monoallyl PQQ Ester

This example provides a synthesis of monoallyl PQQ ester 1 (i.e., the compound of formula I wherein $R_1$ is allyl and $R_2$ and $R_3$ are hydrogen). The synthetic scheme is summarized below.

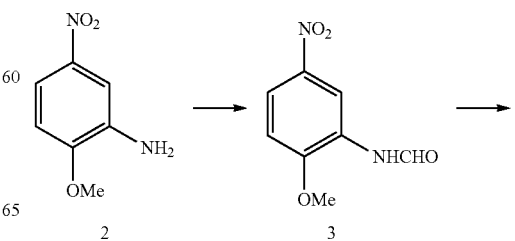

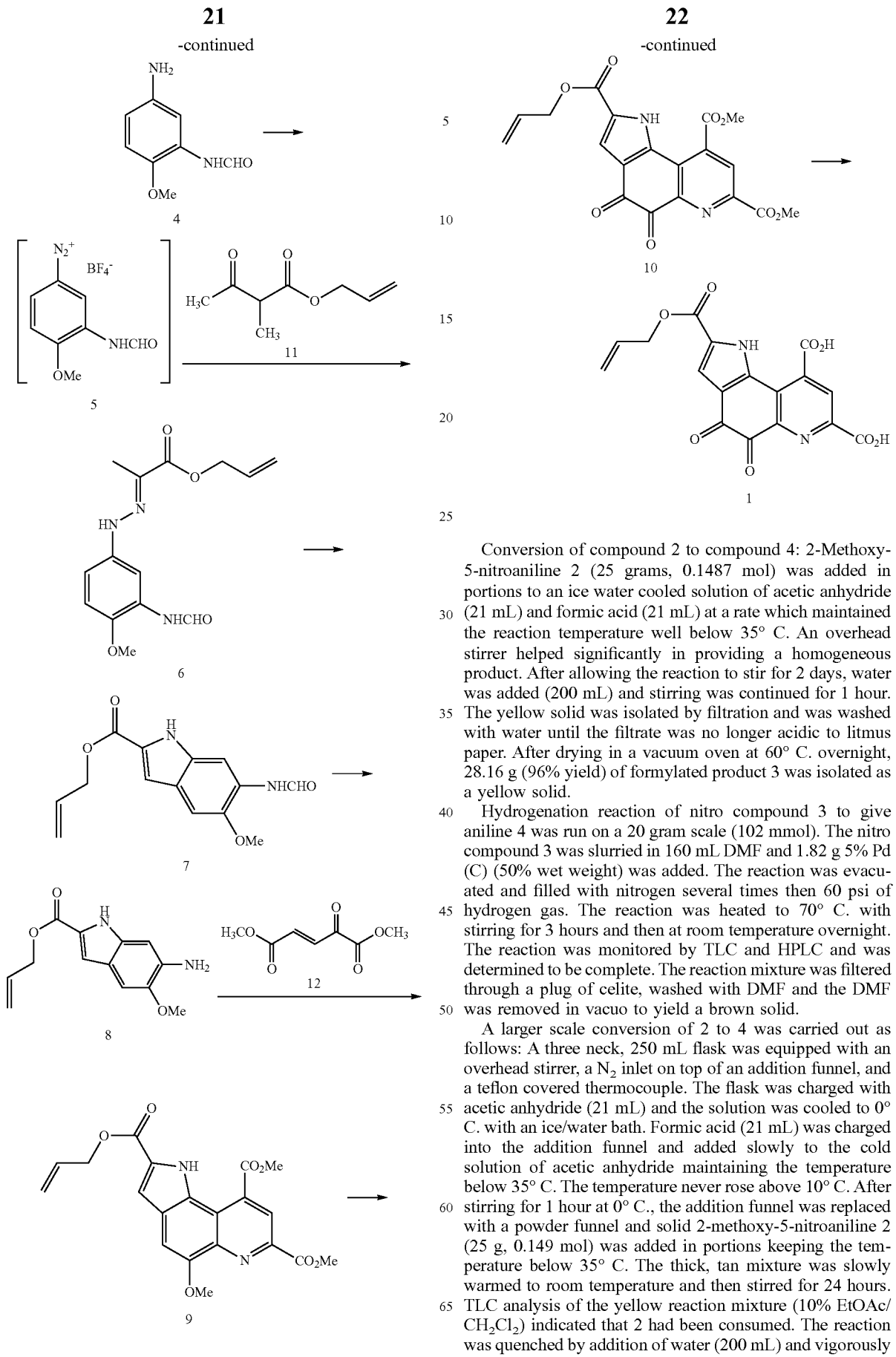

Conversion of compound 2 to compound 4: 2-Methoxy-5-nitroaniline 2 (25 grams, 0.1487 mol) was added in portions to an ice water cooled solution of acetic anhydride (21 mL) and formic acid (21 mL) at a rate which maintained the reaction temperature well below 35° C. An overhead stirrer helped significantly in providing a homogeneous product. After allowing the reaction to stir for 2 days, water was added (200 mL) and stirring was continued for 1 hour. The yellow solid was isolated by filtration and was washed with water until the filtrate was no longer acidic to litmus paper. After drying in a vacuum oven at 60° C. overnight, 28.16 g (96% yield) of formylated product 3 was isolated as a yellow solid.

Hydrogenation reaction of nitro compound 3 to give aniline 4 was run on a 20 gram scale (102 mmol). The nitro compound 3 was slurried in 160 mL DMF and 1.82 g 5% Pd (C) (50% wet weight) was added. The reaction was evacuated and filled with nitrogen several times then 60 psi of hydrogen gas. The reaction was heated to 70° C. with stirring for 3 hours and then at room temperature overnight. The reaction was monitored by TLC and HPLC and was determined to be complete. The reaction mixture was filtered through a plug of celite, washed with DMF and the DMF was removed in vacuo to yield a brown solid.

A larger scale conversion of 2 to 4 was carried out as follows: A three neck, 250 mL flask was equipped with an overhead stirrer, a $N_2$ inlet on top of an addition funnel, and a teflon covered thermocouple. The flask was charged with acetic anhydride (21 mL) and the solution was cooled to 0° C. with an ice/water bath. Formic acid (21 mL) was charged into the addition funnel and added slowly to the cold solution of acetic anhydride maintaining the temperature below 35° C. The temperature never rose above 10° C. After stirring for 1 hour at 0° C., the addition funnel was replaced with a powder funnel and solid 2-methoxy-5-nitroaniline 2 (25 g, 0.149 mol) was added in portions keeping the temperature below 35° C. The thick, tan mixture was slowly warmed to room temperature and then stirred for 24 hours. TLC analysis of the yellow reaction mixture (10% EtOAc/$CH_2Cl_2$) indicated that 2 had been consumed. The reaction was quenched by addition of water (200 mL) and vigorously stirred for 1 h to granulate the precipitated product. The solids were collected by filtration and were washed with water (200 mL aliquots) until the pH of the filtrate was neutral to pH paper. The yellow solid was dried in-vacuo (60° C., 98 mBar) affording 28.2 g (96% yield, 99% pure by HPLC) of compound 3 as a yellow solid. The material obtained was carried into the next step without additional purification. TLC: $R_f$=0.25 (10% EtOAc/CH$_2$Cl$_2$ visualized by UV); LCMS (ESI; M$^{+1}$): 197.1 mu; $^1$H NMR (400 MHz, ppm, d$^6$-DMSO): 10.12 (s, 1H), 9.13 (d, 1H, J=2.7 Hz), 8.38 (d, 1H, J=2.6 Hz), 8.04 (dd, 1H, J=9, 2.7 Hz), 7.28 (d, 1H, J=9 Hz), 4.01 (s, 3H).

An 8 L steel hydrogenation reactor was charged with a slurry containing nitro compound 3 (160.0 g, 0.816 mole), 10% Pd(C) (50% wt by wt water, 12 g, 0.7 mole %) and methanol (3 L). The flask was rinsed twice with methanol (500 mL) and the washes were added to the reactor (total volume of methanol was 4 L). The reactor was evacuated and flushed with nitrogen several times followed by two flushes with hydrogen and finally pressurized to 40 psi with hydrogen. After stirring at room temperature for 1.5 hours, the reaction had not consumed any hydrogen nor did it isotherm. Thus, the pressure was increased to 60 psi and the reaction was warmed to 30° C. During the next 1.5 hours, the reaction started to take up hydrogen (~10 psi) and the internal temperature had risen to 35° C. At this point, the vessel was charged to 65 psi and stirred for 24 hours. After 24 hours, the reaction consumed 45 psi of hydrogen. The vessel was charged back to 65 psi of hydrogen and stirred for 24 hours. Once again the reaction consumed 45 psi of hydrogen and was recharged back to 65 psi and stirred another 24 hours at which time an additional 45 psi of hydrogen had been consumed. The vessel was charged a final time to 65 psi and after 5 hours, only 5 psi of hydrogen was consumed. Thus, the reaction was evacuated, flushed with nitrogen and a sample was removed for analysis by TLC, LC/MS, and HPLC. The analyses indicated that the reaction was complete. The total reaction time at 65 psi was approximately 78 hours. The contents of the reactor were siphoned into a 9 L glass container and then the reactor was flushed three times with methanol (3×1 L). The washes were added to the reaction mixture which was carefully filtered through celite under a flow of nitrogen gas. The liquid level on the filter was never allowed to expose the catalyst during this operation. The celite was washed with methanol (2×250 mL) and the solvent was removed in vacuo to provide aniline 4 (118.5 g) as a tan solid. This material was triturated with iPrOH (100 mL) to provide slightly cleaner material (112 g, 83% yield). TLC: $R_f$=0.10 (10% EtOAc/CH$_2$Cl$_2$ visualized by UV); LCMS (ESI; M$^{+1}$): 167.2 mu; $^1$H NMR (400 MHz, ppm, d$^6$-DMSO): 9.4 (s, 1H), 8.25 (d, 1H, J=2.4 Hz), 7.55 (d, 1H, J=3.0 Hz), 6.73 (d, 1H, J=8.7 Hz), 6.26 (dd, 1H, J=8.7, 2.4 Hz), 4.70 (br s, 2H), 3.70 (s, 3H). There were other small peaks presumably due to the formamide rotamers.

Conversion of compound 4 to compound 6: A 250 mL three neck round bottom flask fitted with an overhead stirrer and thermocouple was charged with concentrated HCl (7.6 mL) and water (1.4 mL) and the flask was cooled to −25° C. with an isopropanol dry ice bath. To this solution was added solid aniline 4 (5 gram, 30.1 mmol) in portions keeping the temperature below −20° C. The thick grey slurry was allowed to stir for 15 minutes and then a solution of sodium nitrite (2.3 grams, 33.3 mmol) in 3.5 mL water was added keeping the reaction temperature below −15° C. The solution was allowed to stir at −15° C. for 30 minutes. Examination of the solution at this point suggested that the diazonium compound 5 had not formed yet, most likely due to the low temperature. A color change was expected upon formation of the diazonium compound. Hence, the bath was removed and the reaction was allowed to warm to 5° C. with careful observation. As the reaction warmed up, the mixture changed from a grey slurry to a red brown solution. The reaction was cooled back to −20° C. and 5 mL of 50% aqueous fluoroboric acid was added over a few minutes. The reaction was warmed slowly to 5° C. and the dark mustard colored diazonium salt 5 was isolated by filtration. The solid was washed with cold ethanol until washings were light in color. The solid was allowed to dry on the vacuum funnel with a stream of nitrogen passing over it.

The diazonium salt 5 was transferred back into the reaction flask and cold ethanol (28 mL) was added. The mixture was cooled to −5° C. with a ice/salt bath and a mixture of sodium acetate (8.2 grams, 100 mmol), water (2.5 mL) and allyl 2-methyl acetoacetate, 11 (4.6 grams, 29.4 mmol) was added over several minutes. The reaction was warmed slowly to room temperature and stirred overnight. Examination of the reaction by TLC indicated that the starting aniline was gone with one major new spot that ran faster than the starting material and appeared to be highly colored. The orange solid hydrazone 6 was isolated by filtration and washed with 200 mL cold 10% ethanol/water and then with 200 mL cold water. The solid was dried in the vacuum oven at 50° C. for several hours. During this time a small sample of the material was analyzed by LC/MS giving a M$^{+H}$ of 292.1 for the desired hydrazone 6. A crude $^1$H NMR was also taken and was consistent with the desired structure.

A second large scale diazotization reaction using 16.4 grams of aniline 4 was also carried out by the same process described above. The two diazotiation/Japp-Klingemann reactions provided 5.92 grams (68% yield) and 18.75 grams (65% yield) of hydrazone 6 as a rust red solid.

Another large scale conversion of 4 to 6 was carried out as follows: A 500 mL three neck round bottom flask fitted with an overhead stirrer, a N$_2$ inlet, and a teflon covered thermocouple was charged with concentrated HCl (25 mL) and water (4.7 mL) and the flask was cooled to −25° C. with an isopropanol dry ice bath. To this solution was added solid aniline 4 (16.4 g, 0.0987 mol) in portions keeping the temperature below −20° C. The thick grey slurry was allowed to stir for 15 minutes and then a solution of sodium nitrite (7.6 g, 0.110 mol) in water (11.5 mL) was added keeping the reaction temperature below −15° C. The solution was allowed to stir at −15° C. for 30 minutes. The bath was removed and the reaction was allowed to warm to 5° C. As the reaction warmed up, the mixture changed from a grey slurry to a red brown solution. The reaction was stirred at 5° C. for approximately 10 minutes. Once the red color appeared, the reaction solution was observed closely to make sure gases were not bubbling off indicating decomposition of the diazonium compound.

The reaction was cooled back to −20° C. and 50% aqueous fluoroboric acid (16.5 mL) was added over 10 minutes keeping the reaction temperature below −3° C. The reaction was warmed slowly to 5° C. and the dark mustard colored diazonium salt 5 was isolated by filtration. The solid was washed with cold ethanol until washings were light in color. The solid was allowed to dry on the vacuum funnel with a stream of nitrogen passing over it, for 1 h.

After drying for 1 hour, the diazonium salt 5 was transferred back into the reaction flask and cold ethanol (88.6 mL) was added. The flask was cooled to −5° C. with an ice/salt bath and a mixture of sodium acetate (26.7 g, 3.3 mol), water (79 mL) and allyl 2-methyl acetoacetate, 11 (15.4 grams, 0.0987 mol) was added over several minutes. The reaction was warmed slowly to room temperature and stirred overnight.

The orange precipitate was isolated by filtration and washed with cold 10% ethanol/water (600 mL) and then with cold water (600 mL). The solid was dried in the vacuum oven at 50° C. for 6 hours providing 18.8 grams of hydrazone 6 in 65% yield (98% pure by HPLC). TLC: $R_f$=0.13 (10% EtOAc/CH$_2$Cl$_2$ visualized by UV); LCMS (ESI; M$^{+1}$): 292.1 mu; $^1$H NMR (400 MHz, ppm, d$^6$-DMSO): 9.83 (s, 1H), 9.61 (s, 1H), 8.30 (d, 1H, J=1.8 Hz), 8.23 (s, 1H), 7.00 (d, 2H, J=1.2 Hz), 5.99 (m, 1H), 5.40, (dd, 1H, J=1.7; 17.5 Hz), 5.22, (dd, 1H, J=1.7; 10.6 Hz), 4.66 (m, 2H), 3.80 (s, 3H), 2.05 (s, 3H).

Preparation of compound 11: The allyl beta-keto ester 11 was prepared as shown in the scheme below.

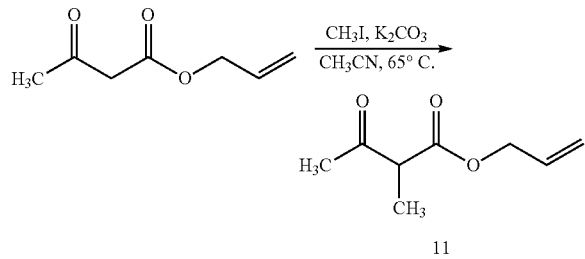

Specifically, allyl acetoacetate (1 gram, 7 mmol), and potassium carbonate (powdered, 1.32 grams, 9 4 mmol) were slurried in either THF or acetonitrile (10 mL) and methyl iodide was added. The reactions were heated in 10° increments starting at 50° C. After one hour at 50° C. and at 60° C., no reaction was seen by TLC. After 2 hours at 70° C., the TLC indicated some reaction was occurring so the reactions were heated at 70° C. overnight. After heating for 18 hours, the reactions were checked by TLC and found to be complete. The reactions were cooled to room temperature and then poured into ice water (30 mL). The volatile solvent was removed in vacuo and the aqueous was extracted twice with ethyl acetate (75 mL). The organic was washed with 0.5 M HCl (50 mL), dried over magnesium sulfate, filtered and concentrated to provide allyl 2-methylacetoacetate, 11 as an orange oil. The reaction in THF gave a 73% yield and the acetonitrile reaction gave a somewhat better yield of 80%. By $^1$H NMR the dialkylated material could only be seen by a singlet for the two methyl groups versus a doublet for the monoalkylated material. Comparison of the integration of the methyl peaks indicated an 8:1 ratio of mono to dialkylation. Since the reaction in acetonitrile gave a better yield, a larger scale reaction was run starting with 25 grams of allyl acetoacetate. Using the same conditions, 29.4 grams of crude allyl 2-methyl acetoacetate was isolated as an orange oil. A true yield could not be calculated since the material contained ethyl acetate. However, the LC/MS and $^1$H NMR indicated that there was approximately 6.5% starting material and 5% dialkylated material in this sample.

A larger scale reaction was carried out as follows: To a three neck round bottom flask equipped with a magnetic stirrer, condenser, and thermocouple was charged potassium carbonate (170 g, 1.23 mol), acetonitrile (1.5L), allyl acetoacetate (100 mL, 0.73 mol), and iodomethane (68.3 mL, 1.09 mol). The reaction was heated to 65° C. monitoring by $^1$H NMR. After 24 hours the $^1$H NMR indicated that there was still 10% starting material present so additional iodomethane (45.6 mL, 0.73 mol) was added and the reaction was heated to 65° C. for an additional 48 hours. The $^1$H NMR showed 86% monoalkylated product 11, 12% dialkylated product and 1% starting material. After cooling to room temperature, the reaction was poured into a stirring solution of cold saturated ammonium chloride (1.8 L). After stirring for 30 minutes, the aqueous solution was extracted with ethyl acetate (2×1 L). The combined organic solution was washed with 0.5 M HCl (2 L), brine (2 L) and dried over magnesium sulfate. After filtration the solution was concentrated to provide 107.6 g of an orange oil which contained allyl 2-methylacetoacetate, 11 (87%), allyl acetoacetate (<1%), and allyl 2,2'-dimethylacetoacetate (13%) as determined by $^1$H NMR. These values were used to calculate how much desired product 11 was produced (93.6 g, 84% yield). TLC: $R_f$=0.44 (20% EtOAc/hexanes, quickly visualized by I$_2$ stain); LCMS (ESI; M$^{+1}$): 157.2 mu ($R_f$=2.5 min, 11), 171.0 mu ($R_f$=4.5 min, allyl 2,2'-dimethylacetoacetate); $^1$H NMR (400 MHz, ppm, CDCl$_3$): 5.91 (m, 1H), 5.33, (m, 1H), 5.26 (m, 1H), 4.64, (d, 2H, J=5.9 Hz), 3.53 (m, 1H), 2.25 (s, 3H), 1.36 (d, 3H, J=7.1 Hz).

Conversion of compound 6 to compound 7: A small scale reaction was initially run using the 5.9 grams obtained from the first Japp-Klingemann reaction. A three neck round bottom flask equipped with an overhead stirrer, condenser, and thermocouple was charged with solid 6 (5.9 g, 20.3 mmol) and formic acid (20 mL). The reaction was heated to 80° C. for 18 hours. The dark brown solution was sampled and analyzed by TLC and LC/MS which showed complete reaction of the starting material plus a new less polar spot. The MS gave M$^{+H}$ of 274.9 for the desired product. Following the procedure in the patent (2006/102642), the reaction was cooled to 0° C. and ethanol was added (10 mL). The mixture was stirred for 2 hours but solids did not precipitate as in the patent. Filtration of the mixture gave only a small amount of brown tacky material. The majority of the product was still in the filtrate. Replacement of an ethyl by an allyl apparently changes the solubility of the product. The filtrate was added to water (100 mL) and the product was extracted with ethyl acetate following the process by TLC. The product did extract but a brown tarry material formed in the separatory funnel and clogged the stopcock. This material was found to not be product and was not very soluble in aqueous or organic solvents. The organic layer was washed with water, dried over sodium sulfate, filtered and concentrated to give 4.45 grams of impure indole 7 as a brown tacky solid.

A second, larger reaction was performed using the same process described above. Hydrazone 6 (18 g, 61.8 mmol) and formic acid (600 mL) were heated to 80° C. After 5 hours, the reaction was sampled and found to be complete by TLC. The reaction was cooled to 0° C. and ethanol (100 mL) was added. The mixture was stirred overnight. The reaction was transferred to a 2 L round bottom flask and the formic acid was removed in vacuo. Water (1.2 L) was added, the mixture was cooled in an ice bath and stirred vigorously for 2 hours. The mixture was filtered and the solids were washed several times with water (2×500 mL). Indole 7 was air dried over several days.

A larger scale reaction was carried out as follows: A three neck round bottom flask equipped with an overhead stirrer, condenser, and thermocouple was charged with hydrazone 6 (100.0 g, 0.343 mol) and formic acid (343 mL). The reaction was heated to 80° C. for 7 hours and allowed to cool and stir at RT overnight. The reaction was transferred to a 1 L round bottom flask, and concentrated in vacuo. The brown fluid solids were transferred into a 2 L four neck round bottom flask using 10% ethanol/water. The solids were too sticky to stir well so ethanol was added while breaking up solids with a spatula until the mixture would stir. The mixture was stirred until the solids were such that they could be poured into a 9.5 L flask containing ice cold water (2 L) with stirring. The mixture was stirred for 48 hours at room temperature. The solids were collected by filtration using a large porcelain Buchner funnel with filter paper. The flask was washed with cold water and added to top of funnel The filtration flask was changed and the solids were washed with ether (400 mL). The solids were transferred to a glass dish and dried in a vacuum oven at 30° C. overnight to provide indole 7 (66 g, 70% yield, 77A % pure) as a brown solid. TLC: $R_f$=0.19 (10% EtOAc/CH$_2$Cl$_2$ visualized by UV); LCMS (ESI; M$^{+1}$): 274.9 mu; $^1$H NMR (400 MHz, ppm, d$^6$-DMSO): 11.74 (s, 1H), 9.74 (s, 1H), 8.44 (s, 1H), 8.37 (d, 1H, J=1.7 Hz), 7.19 (s, 1H), 7.08 (d, 2H, J=1.2 Hz), 6.45 (m, 1H), 5.43, (dd, 1H, J=1.4; 17 Hz), 5.28, (dd, 1H, J=1.4; 10.5 Hz), 4.77 (d, 2H, J=1.8 Hz), 3.87 (s, 3H).

Conversion of compound 7 to compound 8: A 250 mL three neck round bottom flask fitted with a condenser, overhead stirrer, thermocouple and nitrogen inlet was charged with acetone (91 mL), concentrated HCl (4.34 mL), and water (9.1 mL). To this solution was added indole 7 as a solid (3.72 g, 13.56 mmol) and the reaction was refluxed for 1.5 hours. A sample was removed, basified and extracted for TLC and LC/MS analysis. The starting material was gone and a new peak was seen for the desired compound, aniline 8. The reaction was cooled to 0° C. and stirred for 2 hours. The solution was concentrated to remove the acetone. The mixture remained a dark brown color with tacky tar like solids. The solids were scratched from the sides of the flask at which point solid began to form. Continued scratching and stirring provided a tan solid (believed to be the hydrochloride salt) which was isolated by filtration. The yield was 33%. The tan solid was dried overnight and stirred with aqueous sodium hydroxide (2 M) resulting in formation of a different solid, believed to be the basified solid. The initial filtrate was cooled in an ice bath and carefully basified with 2 M NaOH till pH around 8-10 using litmus paper. A tan solid formed and after stirring a foam formed. The solid was filtered but remained tacky and wet. This material was dissolved in methylene chloride and washed with water and brine. After drying over magnesium sulfate the compound was filtered and concentrated to give 1.28 g of material.

A large scale reaction was run, following the same procedure as for the small scale, using 12 grams (43.75 mmol) of indole 7. After about 1 hour of reflux, a sample was removed and the acetone was distilled off The solution was cooled and slowly basified with good stirring. A tan solid precipitated and was isolated by filtration. The solid was examined by TLC and LC/MS and appeared to be aniline 8. Thus after 1.5 hours of reflux, the reaction was concentrated to remove all of the acetone and then cooled to 0° C. Using the moles of HCl used, a slight excess of 5 M sodium hydroxide was slowly added dropwise keeping the temperature below 8° C. A tan solid precipitated. The mixture was stirred cold for three hours and then filtered using a Buchner funnel and filter paper. The solid was dried in the vacuum oven at 60° C. The solid was determined to be 86% pure by HPLC and was purified further by chromatography on a Biotage 340 g SNAP column eluting with a 2-20% gradient of ethyl acetate/methylene chloride. Three sets of fractions containing the desired aniline 8 were isolated to provide a total of 3.2 g (>96%) and a fourth fraction containing 437 mg of less pure material (89%) giving an overall yield of 34% for the two steps.

A larger scale reaction was carried out as follows: A three neck, 5 L flask equipped with an overhead stirrer, a N$_2$ inlet, and a Teflon covered thermocouple was charged with indole 7 (300 g, 1.09 mol) and IPA (1.37 L). A titrated solution of 5M HCl in IPA (2.19 L) was added and the reaction was stirred at room temperature until complete by HPLC analysis, approximately 20 hours. The reaction was diluted with ether (1 L) and the heterogeneous mixture was poured into a stirring solution of ether (2.5 L). The mixture was stirred under nitrogen overnight. Solid 8 HCl was collected by filtration, washed with ether (1 L), dried several hours using a flow of nitrogen, and then transferred to a large glass dish and air dried overnight yielding 8 HCl as a tan solid (305 g, 99% yield). HPLC: $R_t$=4.78 min; LCMS (ESI; M$^{+1}$): 246.9 mu; $^1$H NMR (400 MHz, ppm, d$^6$-DMSO): 12.04 (d, 1H, J=1.4 Hz), 10.02 (br s, 2H), 7.66 (s, 1H), 7.35 (s, 1H), 7.16 (t, 1H, J=1.1 Hz), 6.06 (m, 1H), 5.44 (d of m, 1H), 5.30 (d of m, 1H), 4.83 (m, 2H), 3.91 (s, 3H).

The 8 HCl salt (305 g, 1.0 mol) and water (4 L) were charged into a 9.5 L carboy. The heterogeneous mixture was stirred for 1 hour. A solution of 1M K$_2$HPO$_4$ (1.9 L) was added over a 15 minute period until the pH of the solution was approximately 7. During addition of the phosphate solution, a change in the color and consistency of the aqueous mixture of aniline 8 occurred: it was initially a light tan color and upon basification changed to a light brown mixture. The solution was allowed to stir for several hours. Solid aniline 8 was collected by filtration, washed with water (1L) and dried in a vacuum oven at 50° C. overnight to yield 8 (262 g, 97% yield from 7) as a light brown solid. HPLC: $R_t$=4.78 min; LCMS (ESI; M$^{+1}$): 246.9 mu; $^1$H NMR (300 MHz, ppm, CDCl$_3$): 8.68 (br s, 2H), 7.12 (d, 1H, J=2.3 Hz), 6.94 (s, 1H), 6.63 (s, 1H), 6.04 (m, 1H), 5.44 (d of m, 1H), 5.33 (d of m, 1H), 4.81 (m, 2H), 4.04 (br s, 2H), 3.89 (s, 3H); $^{13}$C NMR (75 MHz, ppm, d$^6$-DMSO): 161.0, 147.6, 133.0, 131.7, 128.6, 126.5, 120.4, 118.5, 108.7, 108.1, 103.5, 65.3, 56.6.

Conversion of compound 8 to compound 9: The next step in the synthesis of PQQ ester is a Doebner-Miller reaction which involves reaction of an aniline with an α,β-unsaturated carbonyl compound. The reaction scheme for this step is shown below.

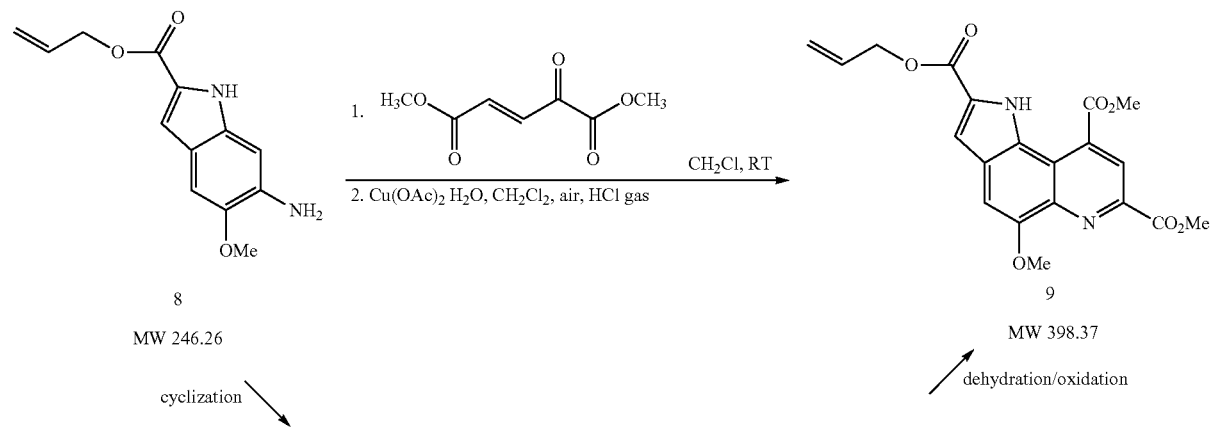

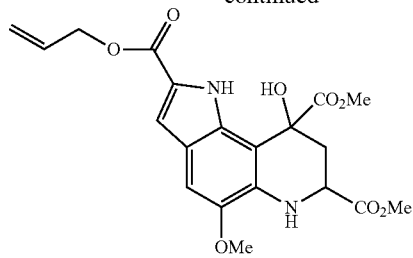

13
MW 418.4

To a solution of aniline 8 (437 mg, 1.77 mmol) in methylene chloride (2.6 mL) was added dimethyl 2-oxo glutaconate 12 (341 mg, 1.98 mmol) in methylene chloride (1.4 mL). The dark colored solution was allowed to stir at room temperature overnight. The solution was concentrated to ¼ of the original volume and placed in an ice bath. A solid precipitated and was collected by filtration and washed with a 1:5 mixture of methylene chloride/hexanes to give compound 13 (400 mg, 54% yield) as a light yellow solid. $^1$H NMR, and LC/MS analyses were consistent for compound 13.

Three dehydration/oxidation reactions were run using this material. Compound 13 (115 mg, 0.28 mmol) was dissolved in methylene chloride (1.6 mL) and then HCl was added keeping the equivalents the same for each reaction (3.9 equivalents): (1) concentrated HCl (100 µl), (2) 5 M HCl in isopropanol (240 µL), and (3) 4 M HCl in dioxane (300 µL). The reactions were all left open to air without addition of the copper acetate. Upon addition of acid, the reactions became darker in color. The reaction using concentrated HCl became very thick and hard to stir. The reactions were examined after 1.5 hours at room temperature by HPLC and LC/MS and again after 18 hours. The HPLC chromatographs looked almost identical for the two time points. All three reactions produced the desired quinoline 9, but still contained some starting material as well as other impurities. The reactions were quenched with bicarbonate, extracted with methylene chloride, dried over magnesium sulfate, filtered and concentrated. $^1$H NMR analysis confirmed the structure of the product quinoline 9, particularly from the NMR of the concentrated HCl reaction. The other two reactions contained significant amounts of starting material compound 13. These experiments established that other HCl sources can be used.

To evaluate the effect of adding copper acetate to drive the oxidation reaction, compound 13 (130 mg, 0.31 mmol) was dissolved in methylene chloride (2 mL). Concentrated HCl (100 µL) and copper sulfate monohydrate (68 mg, 0.34 mmol) were added. The reaction was left open to air and stirred at room temperature for 2 hours. A sample was removed, quenched with bicarbonate solution and extracted into methylene chloride. The solvent was blown off with a stream of nitrogen and analyzed by LC/MS. There was only a small quantity of starting material remaining. The remainder of the material was the desired product, quinoline 9. The reaction was allowed to stir an additional hour and then worked up as before. The reaction produced a significant quantity of solids, believed to be copper salts, that desirably are filtered off The isolated solid quinoline 9 was 96% pure by HPLC and the $^1$H NMR looked very clean. The yield was 50% (60 mg).

A larger scale reaction was carried out as follows: A three neck 500 mL flask was equipped with an overhead stirrer, a $N_2$ inlet, and an addition funnel The reaction flask was charged with aniline 8 (17.2 g, 0.070 mol) and methylene chloride (85 mL). A solution of 12 (14.5 g, 0.084 mol) in methylene chloride (40 mL) was added dropwise to the stirring solution of 8 over 15 minutes. The reaction was stirred at room temperature while monitoring by HPLC. After 2 hours, formation of intermediate 13 was almost complete (5A % 8 and 88A % 13).

To initiate dehydration, concentrated HCl (1.5 mL) was added to the reaction dropwise. A gas spurge tube connected to in-house air was submerged in the solution and air was gently bubbled into the solution. The addition funnel was replaced with a reflux condenser open to air but with water running through it. After 3 hours of bubbling, HPLC analysis indicated formation of 15A % of quinoline 9 and 79A % of intermediate 13. Bubbling of air was continued for an additional 2 hours and then the bubbler was replaced with a nitrogen inlet and the reaction was stirred at room temperature for four days. HPLC analysis indicated the reaction was complete.

The dark brown reaction mixture was poured into a stirring solution of saturated sodium bicarbonate (500 mL) and methylene chloride (500 mL) and the mixture was stirred for an hour. The stirring was stopped to see if separable layers had formed. Although the organic layer was cloudy, the layers were separable. The aqueous layer was extracted twice with methylene chloride (500 mL) and the combined organic layer was dried over sodium sulfate with stirring overnight. A fritted funnel containing a two inch pad of pre-wetted celite was used to filter off the drying agent. The solvent was evaporated to yield a mustard yellow solid (27 g, impure crude 9). The solid was purified by performing a "swish" with methanol (500 mL) yielding after filtration quinoline 9 as a dark yellow solid (18 g, 64% yield, 99A % pure). HPLC: $R_t$=9.1 min; LCMS (ESI; $M^{+1}$): 398.9 mu; $^1$H NMR (400 MHz, ppm, CDCl$_3$): 12.26 (s, 1H), 8.97 (s, 1H), 7.35 (s, 1H), 7.32 (m, 1H), 6.09 (m, 1H), 5.50 (m, 1H), 5.35 (m, 1H), 4.91 (m, 2H), 4.17 (s, 3H), 4.13 (s, 3H), 4.10 (s, 3H); $^{13}$C NMR (75 MHz, ppm, CDCl$_3$): 184.0, 168.6, 165.4, 160.8, 150.7, 143.8, 142.1, 132.3, 131.9, 127.9, 127.6, 124.2, 118.4, 117.4, 110.0, 108.9, 102.9, 65.6, 56.4, 53.9, 53.3. Intermediate 13: HPLC : $R_t$=7.7 min for 13; $^1$H NMR (300 MHz, ppm, d$^6$-DMSO): 9.35 (s, 1H), 7.04 (m, 2H), 6.60 (s, 1H), 6.04 (m, 1H), 5.40 (m, 1H), 5.27 (m, 1H), 4.78 (d, J=5.3 Hz, 2H), 4.09 (br m, 2H), 3.85 (s, 3H), 3.70 (s, 3H), 3.56 (s, 3H), 2.50 (m overlaps with DMSO peak), 2.32 (m, 1H); $^{13}$C NMR (75 MHz, ppm, d$^6$-DMSO): 174.6, 172.3, 160.4, 143.7, 134.2, 132.9, 130.9, 123.1, 117.8, 117.7, 109.2, 102.8, 101.3, 70.8, 64.3, 55.7, 52.6, 52.1, 50.3, 36.7.

Preparation of compound 12: Dimethyl 2-oxoglutaconate 12 was prepared according to a method published by C. Thompson and coworkers (J. Med. Chem. 2002, 45, 2260), shown in the scheme below.

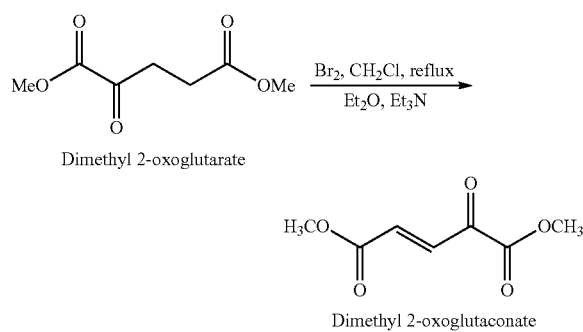

Dimethyl 2-oxoglutarate (6 g, 34.5 mmol) was reacted with bromine (8.5 mL, 0.166 mmol) in methylene chloride. After careful concentration of the solution in vacuo (HBr distills along with the methylene chloride) the bromide was dissolved in ether and eliminated by addition of triethylamine (21 mL) providing 5.53 grams of 12 in a 93% yield.

A scaled up bromination reaction was carried out as follows: A four neck 12 L round bottom flask, fitted with overhead stirrer, condenser, addition funnel topped with a $N_2$ inlet, and a teflon covered thermocouple, was placed in a heating mantle. The condenser was cooled to 5° C. A nitrogen gas adapter was placed on top of the addition funnel and a similar glass adapter was placed on top the condenser and connected to a series of three traps: an empty trap and two traps containing 1M sodium hydroxide solutions. The reaction vessel was charged with dimethyl 2-oxoglutarate (170 mL, 1.17 mol) and methylene chloride (4.76 L). A solution of bromine (72.4 mL) in methylene chloride (340 mL) was added to the addition funnel and then the reaction solution was heated to reflux. Upon reaching reflux, the bromine solution was then added to the reaction mixture dropwise over ~2 hours. Upon complete addition of the bromine solution, the reaction was refluxed for an hour and then checked by 1H NMR. Upon completion, the reaction was cooled to room temperature and excess bromine and HBr vapors were purged from the system and by increasing the nitrogen flow for several minutes. The solution was transferred to a round bottom flask and evaporated providing a orange oil. To remove residual bromine and HBr, the oil was dissolved in additional methylene chloride and evaporated several times.

The bromide compound was transferred back into the 12 L four neck round bottom flask using ether (6 L) to aide in the transfer. The flask was fitted with an overhead stirrer, an addition funnel topped with a $N_2$ inlet, and a Teflon covered thermocouple. A solution of triethylamine (179 mL) in ether (300 mL) was charged into the addition funnel and was added dropwise to the stirring ethereal bromide solution. As the amine was added, solid triethylamine hydrogen bromide precipitated from solution resulting in an orange colored slurry. The reaction was stirred at room temperature for an hour and then checked by $^1$H NMR for completion. The reaction mixture was filtered through 5 L of silica gel using a 6 L course sintered glass funnel and a vacuum flask. The silica was flushed with additional ether (2 L) and the solution of dimethyl 2-oxoglutaconate, (12) was dried over magnesium sulfate, filtered, and concentrated producing a bright yellow crystalline solid (164 grams, 81% yield). LCMS (ESI; M$^{+1}$): 173.1 mu; $^1$H NMR (300 MHz, ppm, CDCl$_3$): 7.64 (d, J=16 Hz, 1H), 6.98 (d, J=16 Hz, 1H), 3.94 (s, 3H), 3.85 (s, 3H); $^{13}$C NMR (100 MHz, ppm, CDCl$_3$): 182.2, 165.1, 160.9, 135.4, 134.1, 53.4, 52.6. Bromide intermediate: $^1$H NMR (300 MHz, ppm, CDCl$_3$): 5.40 (dd, J=9; 6 Hz, 1H), 3.96 (s, 3H), 3.72 (s, 3H), 3.35 (dd, J=17; 9 Hz, 1H), 3.06 (dd, J=17; 6 Hz, 1H).

Conversion of compound 9 to compound 10: Quinoline 9 (220 mg, 0.55 mmol) was slurred in acetonitrile (10 mL) and cooled to −5° C. A solution of cerium ammonium nitrate (CAN) (1.67 g, 3.04 mmol) in water (2.5 mL) was added dropwise and the mixture was stirred at −5° C. for 1.5 hours. The orange reaction was poured into cold water (20 mL) and extracted three times with methylene chloride (3×20 mL). The sample was dried and concentrated to give 145 mg of triester 10 as a red solid (66% yield). This material was examined by HPLC, LC/MS and $^1$H NMR and the desired compound o-quinone 10 was determined to be the major component (73% by HPLC).

A larger scale reaction was also carried out as follows. To a three neck round bottom flask was added 9 (1.5 g, 3.77 mmol) and acetonitrile (70 mL). The slurry was cooled to −5° C. and a solution of CAN (11.35 g, 20.7 mmol) in water (16 mL) was added via an addition funnel over 10 minutes. The bright orange solution was stirred at −5° C. for 1 hour and a sample was removed and analyzed by TLC and LC/MS. The starting material was consumed and the major component gave a MS peak at 6.89 mins with a M$^{+H}$ of 398.8. The reaction was quenched by pouring into ice water (160 mL) and allowed to stir for 30 minutes. A tacky red solid was isolated upon filtration. The tacky solid was dissolved in methylene chloride and washed with water and then brine. The methylene chloride extract was dried over magnesium sulfate, filtered and concentrated to a red solid. The aqueous filtrate was extracted with methylene chloride (3×150 mL), dried over magnesium sulfate, filtered and concentrated to a red solid.

Yet another larger scale reaction was also carried out as follows. To a three neck round bottom flask was added 9 (100 g, 0.25 mol) and 4:1 acetonitrile:water (2 L). The slurry was cooled to −2° C. and a solution of CAN (550 g, 1.0 mol) in water (1 L) was added via an addition funnel while the reaction was cooled over 1.5 hours, while keeping the reaction temperature below 5° C. The mixture was stirred with cooling for an additional 30 minutes and then diluted with ethyl acetate (4 L) and water (1 L) and passed through celite to remove unwanted cerium solids. The solution was transferred to a large extractor and the layers were separated. The aqueous layer was extracted with ethyl acetate (2 L) and the combined organic layer was washed with water (4 L). The organic layer was dried with sodium sulfate and magnesium sulfate, filtered and concentrated under reduced pressure to produce a dark red tacky solid which was triturated with 1:1 toluene/ethyl acetate (200 mL) overnight. After cooling in an ice bath for 1 hour, the solids were collected by filtration, washed with cold 1:1 toluene/ethyl acetate (60 mL) followed by cold methyl tert-butyl ether (MTBE) (2×0.40 ml), and dried in a vacuum oven at 40° C. overnight to yield 57.5 g (58% yield) of >94% pure 10. HPLC: R$_t$=9.8 min, broad peak; LCMS (ESI; M$^{+1}$): 399.1 mu; $^1$H NMR (400 MHz, ppm, CDCl$_3$): 12.99 (br s, 1H), 8.89 (s, 1H), 7.50 (m, 1H), 6.03 (m, 1H), 5.47 (dd, J=17.2; 1.6 Hz, 1H), 5.35 (dd, J=10.6; 1.2 Hz, 1H), 4.86 (m, 2H), 4.18 (s, 3H), 4.07 (s, 3H); $^{13}$C NMR (100.6 MHz, ppm, CDCl$_3$): 184.2, 179.1, 173.0, 167.3, 164.1, 159.5, 148.0, 147.6, 133.8, 133.7, 131.5, 130.8, 128.4, 128.2, 125.6, 119.2, 66.3, 55.1, 53.8.

Conversion of compound 10 to compound 1: The final step in the synthesis of the 2-allyl ester of PPQ, 1, involves selective hydrolysis of the two methyl esters without hydrolysis of the allyl ester. Hydrolysis of triester 10 (20 mg) with LiOH produced the desired compound 1 as confirmed by LC/MS and $^1$H NMR.

Alternatively, a three neck flask was charged with triester 10 (50 g) and acetonitrile (6.28 L) and 0.1 M potassium carbonate (3.14 L) was added through an addition funnel over one hour with stirring to produce the desired compound 1. During addition of potassium carbonate, the reaction color changed from orange to dark brown. The addition funnel was replaced with a condenser and the reaction was heated to 60° C. for 1.5 hours until HPLC confirmed the reaction was complete. The reaction mixture was then placed in an ice bath and cooled over 1 hour to reach 5° C. The condenser was replaced with a 1 L addition funnel containing 500 mL of HCl (2M). The HCl was added dropwise until the pH of the solution remained stable around 1.8-2. During acidification, the reaction color changed from dark brown to orange with red solids precipitating from solution.

The reaction mixture was filtered and a dark red solid was collected and washed with 50 mL cold water followed by 100 mL cold methyl tert-butyl ether (MTBE) and dried in a vacuum oven at 55° C. overnight to produce 41.2 g (89% yield, 94% pure). The obtained solid was recrystallized twice from DMSO/water and dried in a vacuum oven. The yield was 80-90% (99% pure). The product was characterized as follows: HPLC: $R_t$=6.2 min, broad peak; LCMS (ESI; $M^{+1}$): 370.9 mu; $^1$H NMR (400 MHz, ppm, $d^6$-DMSO): 15.60 (br s, 1H), 8.65 (s, 1H), 7.26 (d, J=1.7 Hz, 1H), 6.04 (m, 1H), 5.47 (dd, J=17.2; 1.7 Hz, 1H), 5.30 (dd, J=10.5; 1.2 Hz 1H), 4.81 (dd, J=3.6; 1.5 Hz 2H); $^{13}$C NMR (100.6 MHz, ppm, $d^6$-DMSO): 179.2, 173.7, 168.0, 165.7, 159.8, 148.9, 147.1, 136.9, 132.8, 130.55, 130.52, 126.7, 126.6, 124.2, 118.3, 114.8, 65.4.

Example 2

Synthesis of Monoallyl PQQ Ester

This example provides a synthesis of monoallyl PQQ ester 1 (i.e., the compound of formula I wherein $R_1$ is allyl and $R_2$ and $R_3$ are hydrogen). The synthetic scheme is summarized below.

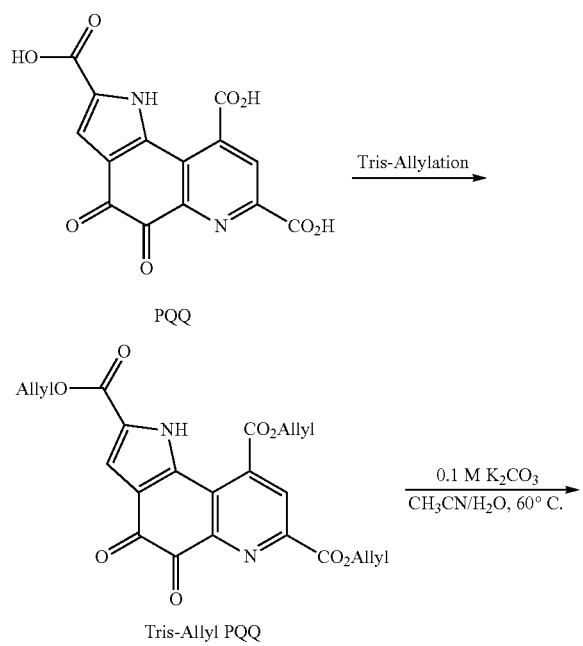

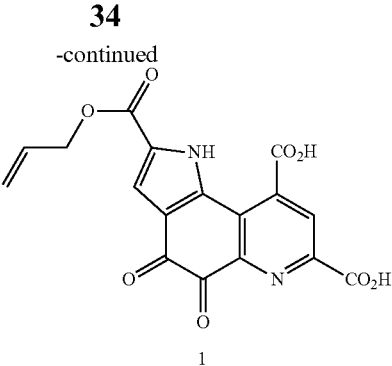

PQQ (100 mg) was reacted with allyl bromide (10 equivalents) and potassium carbonate (8 equivalents) in DMF at 60° C. for 48 hours. Formation of tris-allyl PQQ and 2-allyl PQQ monoester was confirmed by HPLC and NMR.

Example 3

PQQ Ester Compositions

Compositions containing PQQ esters of the present invention should preferably be free of sensitizing-agents (e.g., paraben). Suitable compositions according to the present invention can be prepared with various ingredients, as described below.

Facial Cleanser of the present invention containing: Aqua, Sodium Lauroyl Oat Amino Acids, Sodium $C_{12-16}$ Olefin Sulfonate, Cocamidopropylamine Oxide, Sodium Lactate, PEG-6 Caprylic/Capric Glycerides, Sucrose Polysoyate, PEG-6 Lauramide, Lactic Acid, CI 77891, Glycerin, Glycol Palmitate, Cetearyl Alcohol, Ceteareth-33, PQQ Ester, Salicylic Acid, Caprylic/Capric Triglyceride, Coco-Glucoside, Coconut Alcohol, Cucumis Sativus Fruit Extract, PEG-120 Methyl Glucose Dioleate, Hydroxyethylcellulose, Aluminum Hydroxide, Stearic Acid, Xanthan Gum, Citric Acid, Disodium EDTA, and Phenoxyethanol.

Eye Serum of the present invention containing: Aqua, Sodium Lactate, Isopropyl Lauroyl Sarcosinate, PPG-3 Benzyl Ether Myristate, Algae Extract, CI 77891, Glycerin, Palmitoyl Tripeptide-3, Glycerine, Lactic Acid, Decenel-Butene Copolymer, Caffeine, PQQ Ester, Retinol, Chondrus Crispus, Phenyl Trimethicone, Cyclopentasiloxane, Phospholipids, Dimethiconol, Xanthan Gum, Glucose, Aluminum Hydroxide, Hydrated Silica, Alginic Acid, CI 77489, Silica, Sodium Polyacrylate, PVMIMA Copolymer, Cetearyl Olivate, Sorbitan Olivate, C20-22 Alkyl Phosphate, C20-22 Alcohols, Polysorbate 20, Acrylamide I Sodium Acryloyldimethyl Taurate Copolymer, Isohexadecane, Polysorbate 80, Hydroxyethylcellulose, Triethanolamine, Disodium EDTA, and Phenoxyethanol.

Moisturizing Facial Cream of the present invention containing—: Aqua, Sodium Lactate, 10 Caprylic/Capric Triglyceride, Bis-Hydroxyethoxypropyl Dimethicone, Glycerin, Isopropyl Lauroyl Sarcosinate, Lactic Acid, Cetearyl Glucoside, Glycine Soja Protein, Oxido Reductases, PQQ Ester, Retinol, Sodium Hyaluronate, Sodium PCA, Urea, Trehalose, Chondrus Crispus, Glucose, Isohexadecane, Polyquaternium-5 1, Sodium Polyacrylate, PVMIMA Copolymer, Xanthan Gum, Cetearyl Olivate, Sorbitan Olivate, Glyceryl Stearate, PEG-100 Stearate, Polysorbate 20, Acrylamide 1 Sodium Acryloyldimethyl Taurate Copolymer, Polysorbate 80, Hydroxyethylcellulose, Magnesium Aluminum Silicate, Steareth-100, CI 77891, Hydrogenated Glyceridic Oil, Disodium EDTA, and Phenoxyethanol.

Treatment Peel of the present invention containing: Lactic Acid, Aqua, SD Alcohol 40-B, Ammonium Lactate, Salicylic Acid, PQQ Ester, and Hydroxyethylcellulose.

Alternative composition (e.g., cream) of the present invention containing: Aqua, Glycerin, Cetyl Ricinoleate, Isohexadecane, Ceresin, Glyceryl Stearate, Isopropyl Lauroyl Sarcosinate, Sericin, Dimethicone, PEG-60 Hydrogenated Castor Oil, Steareth-2, Sodium PCA, PEG-100 Stearate, CI 77891, PQQ Ester, Cholesterol, Ceramide 111, Linoleic Acid, Linolenic Acid, Tocopherol, Panicum Miliaceum Extract, Glycosaminoglycans, BHT, Propylene Glycol, Styrene Acrylates Copolymer, Hydrolyzed Corn Starch, Ammonium Hydroxide, PEG-30 Dipolyhydroxystearate, Cetyl Hydroxyethylcellulose, Xanthan Gum, Magnesium Aluminum Silicate, Disodium EDTA, and Phenoxyethanol.

Alternative composition (e.g., cream) of the present invention containing—: Aqua, Sodium Lactate, Glycerin, Sucrose Cocoate, Lactic Acid, Isohexadecane, Isopropyl Lauroyl Sarcosinate, Glyceryl Stearate, PEG-100 Stearate, Sorbitan Stearate, Steareth-2, CI 77891, Magnesium Aluminum Silicate, PEG-60 Hydrogenated Castor Oil, Butylene Glycol, Methyl Dihydroxybenzoate, PQQ Ester, Retinol, Tocopherol, Glycyrrhiza Glabra Root Extract, Moms Alba Leaf Extract, Camellia Oleifera Leaf Extract, Vitis Vinifera Extract, Magnesium Ascorbyl Phosphate, BHT, Bisabolol, Allantoin Glycyrrhetinic Acid, Dimethicone, Polysorbate 20, PEG-30 15 Dipolyhydroxystearate, Xanthan Gum, Cetyl Hydroxyethylcellulose, Disodium EDTA, Propylene Glycol, Styrene Acrylates Copolymer, Hydrolyzed Corn Starch, Ammonium Hydroxide, and Phenoxyethanol.

Sun Protector of the present invention containing: Zinc Oxide, Octinoxate, Oxybenzone, Octisalate, Aqua, Dicaprylyl Carbonate, PEG-20 Stearate, Pentylene Glycol, Glyceryl Stearate, Laureth-23, Silica, Bis-Hydroxyethoxypropyl Dimethicone, Cetearyl Alcohol, Coco-Glucoside, Butyrospermum Parkii Extract, Phospholipids, Cyclopentasiloxane, Cyclohexasiloxane, Butylene Glycol, CapryliclCapric Triglyceride, Ascorbyl Tetraisopalmitate, Tocopherol, Carbomer , Sodium DNA, Cetyl Hydroxyethylcellulose, Potassium Cetyl Phosphate, Hydrogenated Palm Glycerides, Dimethoxydiphenylsilane/Triethoxycaprylylsilane Crosspolymer, Xanthan Gum, Disodium EDTA, Diazolidinyl Urea, and Iodopropynyl Butylcarbamate.

Environmental Protector of the present invention containing: Aqua, Glycerin, Dipropylene Glycol, Glyceryl Stearate, PEG-100 Stearate, Stearyl Alcohol, Ceteareth-20, PQQ Ester, Superoxide Dismutase, Cetyl Hydroxyethylcellulose, Xanthan Gum, Disodium EDTA, and Phenoxyethanol.

Prophetic Composition (e.g., body cream) of the present invention containing at least: PQQ ester, Resveratrol, Xanthin (e.g., Caffeine), AHA (Lactic Acid), and Stimulators of Collagen Synthesis (as, e.g., Vitamin C and derivatives thereof).

Example 4

Environmental Use Test

Two compositions comprising PQQ esters of the invention were tested on women to evaluate the effects of the PQQ ester in promoting positive skin change and reducing detrimental skin change.

Each composition of the invention comprised PQQ ester of formula I where $R_1$ is allyl and $R_2$ and $R_3$ are hydrogen, superoxide dismutase and catalase promoter blend as follows:

| Ingredients | Composition A (Control) | Composition B (Invention) | Composition C (Invention) |
|---|---|---|---|
| PQQ allyl ester | 0% | 0.10% | 0.5% |
| superoxide dismutase catalase promoter: | 0.01% | 0.01% | 0.01% |
| bacopa monniera leaf powder, | 0.10% | 0.10% | 0.10% |
| silybum marianum extract; | 0.10% | 0.10% | 0.10% |
| withania somnifera root extract | 0.10% | 0.10% | 0.10% |

The compositions further comprised water, glycerin, isopropyl lauroyl sarcosinate, cetyl ricinoleate, isohexadecane, ceresin, glyceryl stearate, sericin, C177891, sodium PCA, dimethicone, steareth-2, PEG-100 stearate, PEG-60 hydrogenated castor oil, phenoxyethanol, magnesium aluminum silicate, tocopherol, glycosaminoglycans, PEG-30 dipolyhydroxystearate, xanthan gum, cholesterol, panicum miliaceum extract, cetyl hydroxyethylcellulose, hydrated silica, aluminum hydroxide, BHT, disodium EDTA, linoleic acid, linolenic acid, ethylhexylglycerin, ceramide 3 and alginic acid.

Thirty six women with moderate photodamage between the ages of 43 and 60 were divided into 3 groups. Group 1-3 was asked to apply twice daily (morning and evening) a composition containing 0% PQQ ester (Composition A—control), 0.1% PQQ ester (Composition B—invention), and 0.5% PQQ ester (Composition C—invention), respectively. The women were instructed not to use any other moisturizer during the study period or begin using any new skin care products. The women were allowed to conduct their normal daily activities, including walking, gardening, sports activities etc.

The women were evaluated at baseline and after 6 weeks of use of Compositions A-C for fine lines/wrinkles (photodamage) and vasodilation using RBX photography. The women using Composition A (control) experienced a 33.3% increase in vasodilation as documented by RBX photography compared to 5.3% and 3.8% for the women using Composition B and Composition C, respectively. In addition, the women using Composition A (control) experienced a 9.5% reduction in fine lines and wrinkles (photodamage) compared to 24% and 20% reduction for the women using Composition B and Composition C, respectively.

Vasodilation and photodamage (fine linkes and wrinkles) are directly related to free radical damage associated with sun exposure. As only the control group (Composition A) demonstrated significant increases and vasodilation and only minimal improves in fine lines/wrinkles, these results demonstrate that the PQQ ester compositions of the invention promote positive skin change and reduce detrimental skin change.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments can become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A cosmetic or dermatological composition, comprising:
(i) 0.001 to 0.5 wt. % of a compound of formula (I):

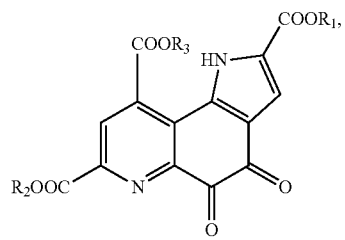

optionally as a salt, wherein $R_1$, $R_2$, and $R_3$ simultaneously or separately represent a $C_{1-6}$ alkyl, $C_{2-6}$ alkenyl, $C_{2-6}$ alkynyl, $C_{4-12}$-ar-$C_{1-6}$-alkyl, $C_{4-12}$-ar$C_{4-12}$-aryl, phenyl, or hydrogen,
(ii) 0.001 to 1 wt. % of superoxide dismutase, and
(iii) a catalase promoter,
wherein the composition is provided in a form of a cream, lotion, solution, serum, anhydrous preparation, emulsion, microemulsion, multiple emulsion, gel, solid stick, ointment, dry powder, spray, or aerosol.

2. The composition of claim 1, wherein $R_1$ is a $C_{2-6}$ alkenyl group, and $R_2$ and $R_3$ are hydrogen.

3. The composition of claim 1, wherein the compound of formula (I) is:

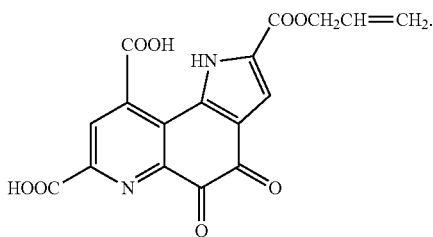

4. The composition of claim 1, further comprising: a catalase.

5. The composition of claim 1, further comprising, based on the weight of the composition: 0.001 wt. % to 2 wt. % of a catalase promoter.

6. The composition of claim 1, further comprising:
a UVA filter, a UVB filter, a skin absorption promoting agent, or a mixture thereof.

7. The composition of claim 1, further comprising:
a second compound of formula (I).

8. The composition of claim 1, having an antioxidant effectiveness that is greater than a composition lacking the compound of formula (I).

9. A method of reducing or eliminating damage from intrinsic skin aging due to declining metabolism, the method comprising:
topically administering to a subject in need thereof the composition of claim 1.

10. The method of claim 9, wherein the damage from intrinsic skin aging due to metabolism comprises decreased collagen production, decreased elasticity of skin, decreased skin thickness, decreased cell turnover, decreased number of blood vessels in the dermis, decreased number of elastins, decreased oil and sweat production, development of benign and malignant skin tumors, formation of age spots, or a combination thereof.

11. A method of improving the appearance of skin, the method comprising:
topically administering to a subject in need thereof the composition of claim 1.

12. A method of stabilizing formulation ingredients in a cosmetic or dermatological composition, the method comprising:
combining the composition of claim 1 with an additive comprising a surfactant, cosmetic auxiliary, pigment, UVA filter, UVB filter, propellant, thickening agent, emulsifier, solvent, water, antioxidant, perfume, dyestuff deodorant, antimicrobial material, back-fatting agent, complexing agent, sequestering agent, pearlescent agent, exfoliating agent, plant extract, vitamin, or mixture thereof,
wherein the composition provides improved stabilization of the additive, and
wherein the composition is in a form of a cream, lotion, solution, serum, anhydrous preparation, emulsion, microemulsion, multiple emulsion, gel, solid stick, ointment, dry powder, or aerosol.

13. The method of claim 12, wherein the additive is an antioxidant comprising vitamin A, a derivate of vitamin A, vitamin B, a derivate of vitamin B, vitamin C, a derivate of vitamin C, vitamin E, a derivate of vitamin E, or a mixture thereof.

14. The composition of claim 3, comprising a catalase promoter.

15. The composition of claim 1, comprising 0.001 to 0.05 wt. % superoxide dismutase, based on the weight of the composition.

16. The composition of claim 3, comprising 0.001 to 0.05 wt. % superoxide dismutase, based on the weight of the composition.

17. The method of claim 9, wherein the damage comprises decreased collagen production.

18. The method of claim 9, wherein the damage comprises decreased elasticity of skin.

19. The method of claim 9, wherein the damage comprises decreased skin thickness.

20. The method of claim 9, wherein the damage comprises decreased cell turnover.

21. The method of claim 9, wherein the damage comprises decreased number of blood vessels in the dermis.

22. The method of claim 9, wherein the damage comprises decreased number of elastins.

23. The composition of claim 1, comprising the compound of formula (I) in the form of a basic salt.

24. The composition of claim 1, wherein $R_1$ is $C_{2-6}$ alkenyl.

25. The composition of claim 1, wherein $R_1$ is a $C_{2-6}$ alkenyl.

* * * * *